(12) United States Patent
Wang et al.

(10) Patent No.: US 10,643,354 B2
(45) Date of Patent: May 5, 2020

(54) AUTOMATIC SYSTEM CALIBRATION METHOD OF X-RAY CT

(71) Applicant: RENSSELAER POLYTECHNIC INSTITUTE, Troy, NY (US)

(72) Inventors: Ge Wang, Loudonville, NY (US); Mianyi Chen, Troy, NY (US); Yan Xi, Syracuse, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 160 days.

(21) Appl. No.: 15/558,053

(22) PCT Filed: Mar. 21, 2016

(86) PCT No.: PCT/US2016/023460
§ 371 (c)(1),
(2) Date: Sep. 13, 2017

(87) PCT Pub. No.: WO2016/154136
PCT Pub. Date: Sep. 29, 2016

(65) Prior Publication Data
US 2018/0068467 A1    Mar. 8, 2018

Related U.S. Application Data

(60) Provisional application No. 62/135,861, filed on Mar. 20, 2015.

(51) Int. Cl.
*G06K 9/00*    (2006.01)
*G06T 11/00*    (2006.01)
(Continued)

(52) U.S. Cl.
CPC ............ *G06T 11/005* (2013.01); *A61B 6/032* (2013.01); *A61B 6/5205* (2013.01); *A61B 6/582* (2013.01);
(Continued)

(58) Field of Classification Search
USPC .................................................. 382/128–134
See application file for complete search history.

(56) References Cited

U.S. PATENT DOCUMENTS 6,332,030 B1 * 12/2001 Manjunath ............ G06T 1/0028
382/100
8,005,184 B2 8/2011 Chen
(Continued)

FOREIGN PATENT DOCUMENTS

EP         2014233        1/2009
WO    2015164405 A1    10/2015
(Continued)

OTHER PUBLICATIONS

Wang et al., "An outlook on x-ray CT research and development," Medical Physics, Mar. 2008, pp. 1051-1064, vol. 35, No. 3.
(Continued)

*Primary Examiner* — Alex Kok S Liew
(74) *Attorney, Agent, or Firm* — Murtha Cullina LLP; Anthony P. Gangemi

(57) ABSTRACT

Systems and methods for geometric calibration and image reconstruction in computed tomography (CT) scanning using iterative reconstruction algorithms are provided. An iterative reconstruction algorithm can be used to reconstruct an improved image, and then the improved image can be used to adjust inaccurate parameters by using a Locally Linear Embedding (LLE) method. Adjusted parameters can then be used to reconstruct new images, which can then be used to further adjust the parameters. The steps of this
(Continued)

iterative process can be repeated until a quality threshold is met.

30 Claims, 37 Drawing Sheets

(51) Int. Cl.
    *A61B 6/03*      (2006.01)
    *A61B 6/00*      (2006.01)

(52) U.S. Cl.
    CPC ... *G06T 11/006* (2013.01); *G06T 2207/10116* (2013.01); *G06T 2207/20* (2013.01); *G06T 2211/412* (2013.01); *G06T 2211/424* (2013.01)

(56) References Cited

U.S. PATENT DOCUMENTS

| | | | |
|---|---|---|---|
| 8,189,735 B2 | 5/2012 | Khare et al. | |
| 9,600,910 B2 | 3/2017 | Wang et al. | |
| 9,730,657 B2 | 8/2017 | Wang et al. | |
| 2005/0141769 A1* | 6/2005 | Ho | G06K 9/6215 382/225 |
| 2007/0276215 A1 | 11/2007 | Ziegler | |
| 2008/0267484 A1* | 10/2008 | Chen | A61B 6/032 382/132 |
| 2010/0135541 A1* | 6/2010 | Lai | G06K 9/00208 382/118 |
| 2012/0088981 A1* | 4/2012 | Liu | G06K 9/6215 600/300 |
| 2012/0219212 A1* | 8/2012 | Anbai | G06F 16/316 382/159 |
| 2015/0030227 A1 | 1/2015 | Liang et al. | |
| 2015/0157286 A1 | 6/2015 | Wang et al. | |
| 2016/0113602 A1 | 4/2016 | Wang et al. | |
| 2016/0135769 A1 | 5/2016 | Wang et al. | |
| 2016/0166852 A1 | 6/2016 | Wang et al. | |
| 2017/0043041 A1 | 2/2017 | Wang et al. | |

FOREIGN PATENT DOCUMENTS

| | | |
|---|---|---|
| WO | 2016106348 A1 | 6/2016 |
| WO | 2016118960 A1 | 7/2016 |
| WO | 2016154136 A1 | 9/2016 |
| WO | 2016197127 A1 | 12/2016 |
| WO | 2017015381 A1 | 1/2017 |
| WO | 2017019782 A1 | 2/2017 |
| WO | 2017048856 A1 | 3/2017 |
| WO | 2017083849 A1 | 5/2017 |
| WO | 2017143247 A1 | 8/2017 |
| WO | 2017176976 A1 | 10/2017 |

OTHER PUBLICATIONS

Wang et al., "Design, analysis and simulation for development of the first clinical micro-CT scanner," Academic Radiology, Apr. 2005, pp. 511-525, vol. 12, No. 4.
Panetta et al., "An optimization-based method for geometrical calibration in cone-beam CT without dedicated phantoms," Physics in Medicine and Biology, Jun. 2008, pp. 3841-3861, vol. 53.
Wein et al., "Self-calibration of geometric and radiometric parameters for cone-beam computed tomography," Eleventh International Meeting on Fully Three-Dimensional Image Reconstruction in Radiology and Nuclear Medicine, Jul. 2011, pp. 1-4.
Patel et al., "Self-calibration of a cone-beam micro-CT system," Medical Physics, Jan. 2009, pp. 48-58, vol. 36, No. 1.
Liu et al., "Half-scan cone-beam CT fluoroscopy with multiple x-ray sources," Medical Physics, Jul. 2001, pp. 1466-1471, vol. 28, No. 7.
Crawford et al., "Computed tomography scanning with simultaneous patient translation," Medical Physics, Nov./Dec. 1990, pp. 967-982, vol. 17, No. 6.
Wang et al., "Preliminary study on helical CT algorithms for patient motion estimation and compensation," IEEE Transactions on Medical Imaging, Jun. 1995, pp. 205-211, vol. 14, No. 2.
Yu et al., "Data consistency based rigid motion artifact reduction in fan-beam CT," IEEE Transactions on Medical Imaging, Feb. 2007, pp. 249-260, vol. 26, No. 2.
Yu et al., "Data consistency based translational motion artifact reduction in fan-beam CT," IEEE Transactions on Medical Imaging, Jun. 2006, pp. 792-803, vol. 25, No. 6.
Leng et al., "Motion artifact reduction in fan-beam and cone-beam computed tomography via the fan-beam data consistency condition (FDCC)," Medical Imaging: Physics of Medical Imaging, Mar. 2007, pp. 1-13.
Roweis et al., "Nonlinear dimensionality reduction by locally linear embedding," Science, Dec. 2000, pp. 2323-2326, vol. 290.
Saul et al., "An introduction to locally linear embedding," Draft version, Jan. 2001, http://www.cs.nyu.edu/~roweis/lle/papers/lleintro.pdf.
Siddon, "Fast calculation of the exact radiological path for a three-dimensional CT array," Medical Physics, Mar./Apr. 1985, pp. 252-255, vol. 12, No. 2.
Wang et al., "A universal image quality index," IEEE Signal Processing Letters, Mar. 2002, pp. 1-4.
Wang et al., "Ordered-subset simultaneous algebraic reconstruction techniques (OS-SART)," Journal of X-Ray Science and Technology, Oct. 2004, pp. 1-10, Draft copy.
Sidky et al., "Accurate image reconstruction from few-views and limited-angle data in divergent-beam CT," Journal of X-Ray Science and Technology, Author copy, Apr. 2009, pp. 1-30.
International Search Report and Written Opinion, International Application No. PCT/US2016/023460, PCT/ISA/210, PCT/ISA/220, PCT/ISA/237, dated Jun. 21, 2016.

* cited by examiner

AUTOMATIC SYSTEM CALIBRATION METHOD OF X-RAY CT

CROSS-REFERENCE TO RELATED APPLICATIONS

The present application is a national stage application of International Application No. PCT/US2016/023460, filed Mar. 21, 2016, which claims the benefit of U.S. Provisional Application Ser. No. 62/135,861, filed Mar. 20, 2015, both of which are incorporated herein by reference in their entirety, including any figures, tables, and drawings.

GOVERNMENT SUPPORT

This invention was made with government support under grant No. R01 EB016977 and U01 EB017140 awarded by National Institutes of Health. The government has certain rights in the invention.

BACKGROUND OF INVENTION

In the medical imaging field, X-ray computed tomography (CT) provides critical diagnostic information. Recently, CT techniques have been developed to provide quality images at low radiation dose. Patient motion or inaccurate machinery can lead to inaccurate projection angles or distance between the X-ray source and the center of the object being scanned, thereby resulting in inaccurate results. Another challenging problem in this field is geometric calibration, such as for C-arm CT and ultra-high resolution CT. This problem is also related to rigid patient motion compensation, because motion is relative between imaging components and a patient body.

To perform geometric calibration and motion correction, a number of methods have been proposed recently. Analytic methods with a calibration phantom and iterative methods with or without a calibration phantom have been proposed. Analytic methods are widely used in industrial CT and can be based on the identification of elliptical parameters in cone-beam geometry. Some calibration methods are iterative, such as optimization-based calibration for cone-beam CT, self-calibration for cone-beam CT, and self-calibration for cone-beam micro-CT. There is an overlap in the literature on geometric calibration and motion reduction. While some motion reduction methods utilize fast scanning, even with multi-source-detector systems or while avoiding motion-affected data, other methods estimate patient motion and compensate for its effect. Each of these methods has limitations, though.

BRIEF SUMMARY

The subject invention provides novel and advantageous systems and methods for geometric calibration and image reconstruction in computed tomography (CT) scanning (e.g., X-ray CT scanning) using one or more iterative reconstruction algorithms. An iterative reconstruction algorithm (e.g., based on Total Variation) can be used to reconstruct an improved image, and then the improved image can be used to adjust inaccurate parameters, for example by using a Locally Linear Embedding (LLE) method. Adjusted parameters can then be used to reconstruct new images, which can then be used to further adjust the parameters. The steps of this iterative process can be repeated until a quality threshold is met. This can lead to automatic system calibration for X-ray CT, as opposed to related art parameter adjustment methods and systems based on accurate but expensive machinery.

In an embodiment, a method of reconstructing a CT image can include: obtaining an initial CT image; performing a reconstruction algorithm on the initial CT image to obtain a reconstructed image of the initial CT image; using the reconstructed image to adjust one or more parameters associated with the image (e.g., using an LLE method); using the adjusted one or more parameters to perform the reconstruction algorithm on the reconstructed image to obtain an updated reconstructed image; and iteratively repeating the parameter adjustment and updating of the image reconstructions (using the most-recently updated reconstructed image each time and updating the same one or more parameters each time) until a threshold value of a predetermined characteristic is met.

In a further embodiment, a CT system can include: a radiation source; a detector for detecting radiation from the radiation source; and a computer including a computer readable medium having computer-executable instructions stored thereon for performing a method of the subject invention.

DETAILED DESCRIPTION

Figure 1:
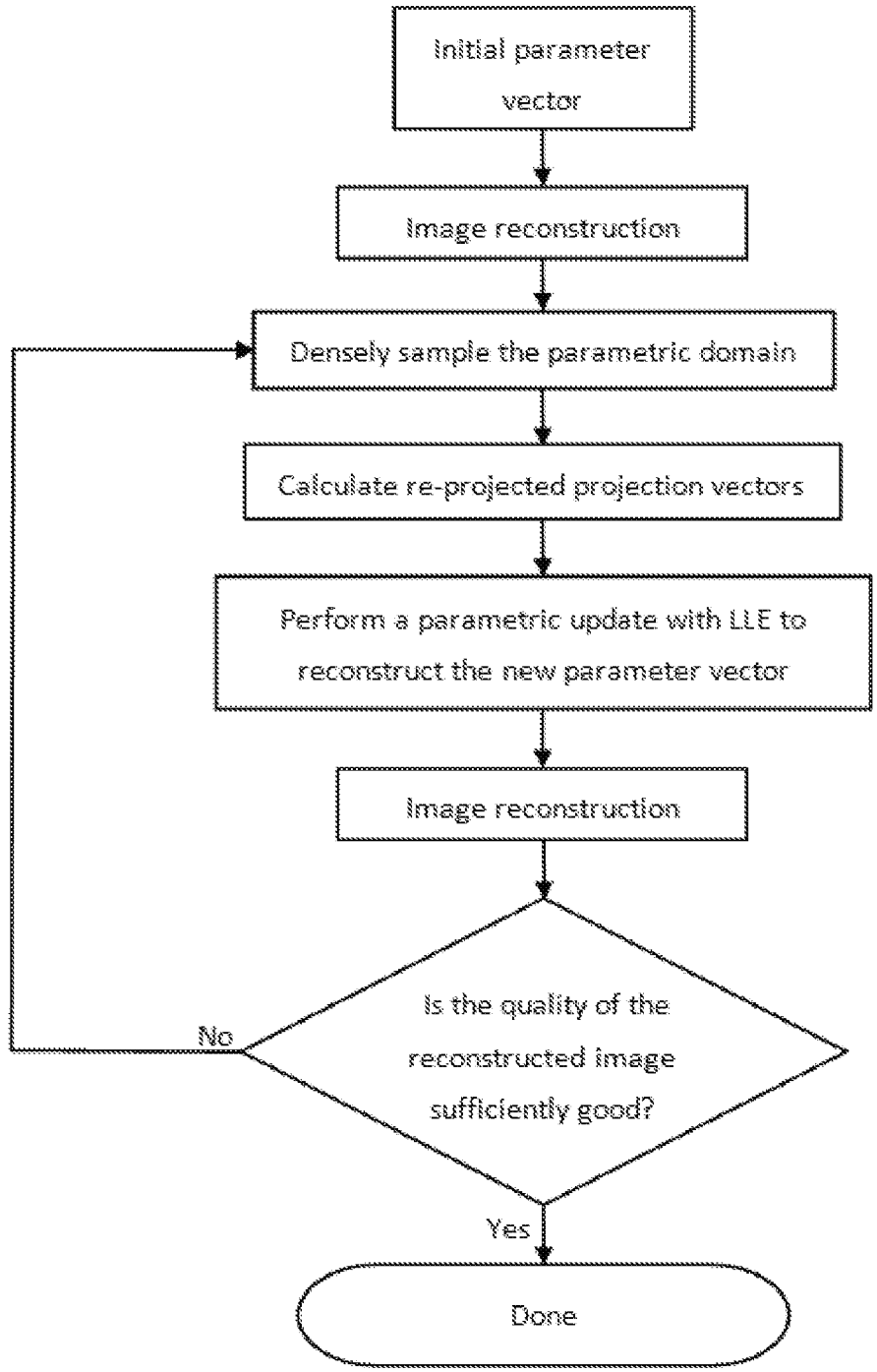
FIG. 1 shows a flow chart of a locally linear embedding (LLE)-based calibration according to an embodiment of the subject invention.

The subject invention provides novel and advantageous systems and methods for geometric calibration and image reconstruction in computed tomography (CT) scanning (e.g., X-ray CT scanning) using one or more iterative reconstruction algorithms. An iterative reconstruction algorithm (e.g., based on Total Variation) can be used to reconstruct an improved image, and then the improved image can be used to adjust inaccurate parameters, for example by using a Locally Linear Embedding (LLE) method. Adjusted parameters can then be used to reconstruct new images, which can then be used to further adjust the parameters. The steps of this iterative process can be repeated until a quality threshold is met. This can lead to automatic system calibration for X-ray CT, as opposed to related art parameter adjustment methods and systems based on accurate but expensive machinery. Thus, methods and systems of the subject invention can significantly decrease costs in X-ray CT. Also, system geometric parameters can be extracted directly from projection data under practical conditions.

Embodiments of the subject invention can adjust inaccurate parameters in CT scanning using a mathematical method, thereby helpfully reconstructing CT images with better quality. Because this method is an iterative method, in an embodiment, parallel calculation (e.g., a GPU method) can be used and can decrease calculation time.

In many embodiments of the subject invention, geometric calibration (e.g., iteratively updating parameters) can be performed on CT scanning (e.g., X-ray CT scanning) by coupling LLE and re-projection. An initial parameterization can be used to reconstruct a CT image, and re-projected projection vectors that sample the parametric range densely can be calculated. With the re-projected projection vectors and the original projection vectors, weight coefficients and neighbors for LLE can be calculated, and the parameter estimation can be updated. An image can be iteratively reconstructed until a satisfactory quality is achieved (for example, until one or more threshold values in one or more characteristics of interest is/are met). In certain embodiments, LLE and re-projection can be used on fan-beam imaging geometry CT scanning.

LLE was proposed in 2000 as an unsupervised manifold learning algorithm for dimensionality reduction (Roweis et al., "Nonlinear dimensionality reduction by locally linear embedding", *Science* 290.5500 (2000): 2323-2326; and Roweis et al., "An introduction to locally linear embedding", http://www.cs.toronto.edu/~roweis/lle/publications.html (2000); both of which are hereby incorporated herein by reference in their entireties). Related to classic dimensionality reduction methods such as principal component analysis (PCA) and multidimensional scaling (MDS), LLE computes eigenvectors but does so locally to preserve intrinsic geometry embedded in a high dimensional space. LLE is easy to implement and yet gives excellent performance when data are sufficiently dense. LLE can include three steps: Step 1 can include finding the K nearest neighbors for each high-dimensional point in terms of the Euclidean distance; step 2 can include representing each point linearly with its neighbors and calculating weight coefficients for its neighbors; and step 3 can include mapping high dimensional data with the weight coefficients to a low dimensional representation on an intrinsic manifold.

In many embodiment of the subject invention, with the data vector $b_i$, the first step of LLE can be to find its K nearest neighbors in its dataset vectors $\tilde{b}_{ij}$ according to the Euclidean distance:

$$d_{ij} = \|b_i - \tilde{b}_{ij}\|_2^2. \tag{1}$$

With the K nearest vectors, the second step can be to represent the original data vector linearly with its neighboring vectors:

$$b_i = \sum_{k=1}^{K} w_{ik} \tilde{b}_{ik}, \tag{2}$$

where $\tilde{b}_{ik}$ are the K nearest neighbors and $w_{ik}$ are respectively weight coefficients, and $$\sum_k w_{ik} = 1.$$

The weight matrix can be solved by minimizing the following error:

$$\min \left\| b_i - \sum_k w_{ik} \tilde{b}_{ik} \right\|_2^2 s.t. \sum_j w_{ik} = 1. \tag{3}$$

Using the constraint $$\sum_k w_{ik} = 1,$$

to solve Equation (3) is equivalent to solving the linear system:

$$\sum_k c_{jk} w_{ik} = 1, \tag{4}$$

where $C=(c_{jk})$ is the local covariance matrix calculated as:

$$C=(b_i-\tilde{b}_{ik})^T(b_i\tilde{b}_{ik}). \quad (5)$$

With the weight coefficients $W=(w_{ik})$, the third step can include calculating the global internal coordinate $Y=(y_i)$ by solving the equation:

$$\min_Y \sum_i \left\| y_i - \sum_k w_{ik} y_k \right\|_2^2. \quad (6)$$

By the Rayleitz-Ritz theorem, the solution of Equation (6) is given by the bottom d+1 eigenvectors of the generalized eigenvalue problem:

$$MY=\lambda Y, \quad (7)$$

where $\lambda$ is the eigenvalue, and $M=(I-W)^T(I-W)$.

Figure 13:
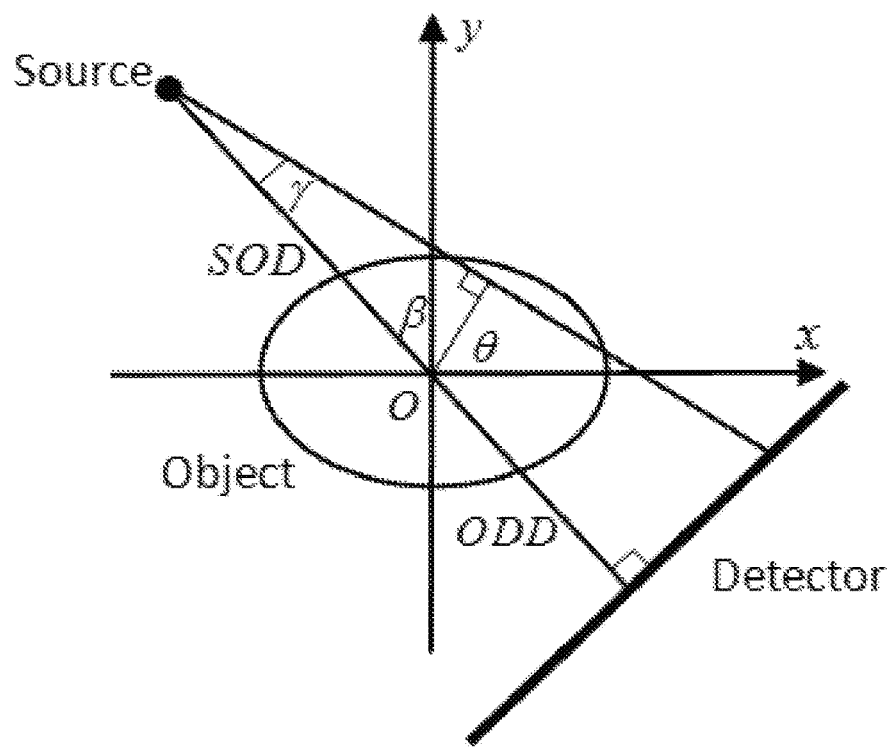
FIG. 13 shows a schematic view illustrating fan-beam geometry for X-ray CT.

FIG. 13 shows a schematic view illustrating fan-beam geometry for X-ray CT, which is popular with commercial spiral CT systems. Referring to FIG. 13, in fan-beam geometry the origin of the Cartesian coordinate system can be the nominal center of an object to be scanned and reconstructed, and the X-ray source is intended to be on a circular trajectory whose center is the origin. The source-to-object distance (SOD) is the distance between the X-ray source and the system origin, which is the radius of the scanning circle. The X-ray source emits fan-beam X-rays covering the object. The central ray in the fan-beam can be perpendicular to a linear detector array of length L which receives X-rays after being attenuated by the object, and the angle between a ray of interest and the central ray can be denoted as γ. The object-to-detector distance (ODD) is the distance between the system origin and the detector midpoint. The symbol θ denotes the X-ray scanning angle, and β=θ−γ.

Because the X-ray source is on a circular trajectory, it can be convenient to represent fan-beam geometry in a polar coordinate system. Various practical factors can lead to inaccurate geometric parameters in a view-dependent fashion. Specifically, inaccurate projection angles and other parameters can include:

$$\hat{\theta}_i=\theta_i+\delta_i, \, i=1,2,\ldots,N, \quad (8)$$

$$\tilde{p}_j=p_j\varepsilon_j, \, j=1,2,\ldots,M, \quad (9)$$

where $\theta_i$ are the accurate projection angles, $p_j$ are the other accurate geometric parameters including SOD, ODD, detector offset, and detector tilt angle, which do not depend on $\theta_i$. N is the number of views, M is the number of other parameters, and $\delta_i$ and $\varepsilon_j$ are respectively the angular error and the parametric error. In general, more accurate geometric parameters will lead to the ability to reconstruct a better CT image.

Figure 14:
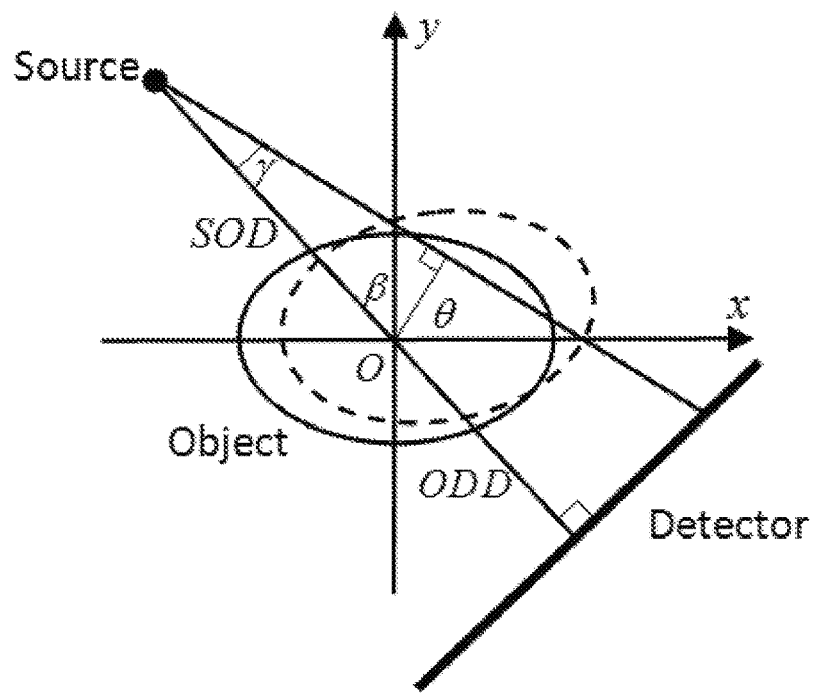
FIG. 14 shows a schematic view illustrating object or patient movement in fan-beam X-ray CT.

A rigid patient motion problem can be present in the geometric calibration during fan-beam geometry CT scanning. FIG. 14 shows a schematic view illustrating object or patient movement in fan-beam X-ray CT. Referring to FIG. 14, patient motion can be represented with an object x-coordinate offset $x_i$, an object y-coordinate offset $y_i$, and a projection angular error, while the projection angle can still be expressed by Equation (8).

In many embodiments of the subject invention, calibration with LLE can be performed. An iterative CT reconstruction approach can be modeled to solve the following linear system of equations:

$$Au=b_i, \quad (10)$$

where $u=(u_1, u_2, \ldots, u_J)$ is an image represented as a J dimensional vector, J is the number of pixels, $b_i=(b_1, b_2, \ldots, b_L)$ is data, L is the number of vector elements, and $A=(a_{jk})$ is a projection matrix related to the geometric parameters. If both the system matrix and projection data are known, an iterative algorithm can be used to reconstruct a CT image with a fixed projection matrix by reducing the difference between original and re-projected data. In a reconstruction algorithm, an important step is to calculate the projection matrix, which is affected by the geometric parameters, such as projection angle and SOD; that is, $$A=A(P), \quad (11)$$

where P is an estimated parameter vector, which includes SOD, ODD and detector offset distance, detector tilt angle, and/or projection angle, possibly among others.

In an embodiment, projections can be calculated using a distance-driven method, such as the distance-driven method disclosed Siddon (Fast calculation of the exact radiological path for a three-dimensional CT array, Medical Physics 12(2) (1985), 252-255), which is hereby incorporated herein by reference in its entirety. Based on the re-projection approach in the iterative reconstruction, a new iterative method can be formulated to estimate the geometric parameters by minimizing the mean squared error between the projection data and re-projected projection data, which can be formulated as:

$$P=\arg\min \|b_i-\tilde{b}_{ij}\|_2^2 \, s.t. \, A(P)u=b_i, \quad (12)$$

where $b_i$ is the projection vector obtained from the measurement along different projection views, $\tilde{b}_{ij}$ is the corresponding re-projected projection vector from a reconstructed image with sampled parameters, and P is the updated vector of parameters. The re-projected projection vector can be calculated by Equations (10) and (11) within a densely sampled parametric range:

$$\tilde{P}_j=(p_{j1},p_{j2},\ldots,p_{jn}). \quad (13)$$

If the parametric sampling interval is sufficiently small, a true parameter vector is close to neighboring sampled parameter vectors, and the measured projection vector can be linearly expressed by the K nearest re-projected projection vectors associated with the sampled parameter vectors. That is, $$b_i = \sum_{k=1}^{K} w_{ik}\tilde{b}_{ik}, \quad (14)$$

$$P = \sum_{k=1}^{K} w_{ik}\tilde{P}_k, \quad (15)$$

where $\tilde{b}_{ik}$ are the K nearest re-projection vectors associated with the corresponding K vectors of parameters $\tilde{P}_k$, and $w_{ik}$ are weight coefficients. The key relationship is that the weight coefficients for Equations (14) and (15) are the same. Therefore, the real parameter estimation can be refined by searching for the K nearest re-projected projection vectors and updating the parameter vector with the weight coefficients and the corresponding sampled parameters. Consequently, the geometric calibration problem can be solved by dimensionality reduction via LLE.

With a densely sampled parametric domain and correspondingly re-projected projection vectors, the K nearest re-projected projection vectors of an original projection vector can be found and the weight coefficients can be calculated with LLE by using Equations (1), (4), and (5). With the sampled parameters and corresponding weight coefficients, a parametric update can be performed according to Equation (15).

FIG. 1 shows a flow chart of an LLE-based calibration according to an embodiment of the subject invention, as discussed in the preceding paragraphs.

In certain embodiments, universal quality index (UQI) can be used to evaluate reconstructed images and/or as a threshold characteristic to determine when an iterative reconstruction process should be stopped. UQI is described in detail in Wang et al. (A universal image quality index, *Signal Processing Letters*, IEEE 9(3) (2002), 81-84), which is hereby incorporated herein by reference in its entirety. In certain embodiments, geometric calibration results can be quantified using the average angular error ($\bar{\theta}_{error}$), parametric error ($P_{Error}$), and/or average object coordinate offsets $\bar{x}$ and $\bar{y}$. These can be used along with UQI or with one or more other threshold characteristics.

The UQI evaluates an image by integrating three factors including correlation distortion, brightness distortion, and contrast distortion. The range of UQI is between −1 and 1. The closer to 1 the UQI, the better a reconstructed image will be. Given a reconstructed image $u^*_{ij}$ and the ground truth image $u_{ij}$ of S×T, the UQI is defined as:

$$UQI = \frac{4\sigma_{uu^*}.\bar{u} \times \bar{u}^*}{(\sigma_u^2 + \sigma_{u^*}^2)[(\bar{u})^2 + (\bar{u}^*)^2]}, \qquad (16)$$

where $$\bar{u} = \frac{1}{S \times T} \sum_{0 \le i < S} \sum_{0 \le j < T} u_{ij}, \qquad (17)$$

$$\bar{u}^* = \frac{1}{S \times T} \sum_{0 \le i < S} \sum_{0 \le j < T} u^*_{ij}, \qquad (18)$$

$$\sigma_u^2 = \frac{1}{S \times T - 1} \sum_{0 \le i < S} \sum_{0 \le j < T} (u_{ij} - \bar{u})^2, \qquad (19)$$

$$\sigma_{u^*}^2 = \frac{1}{S \times T - 1} \sum_{0 \le i < S} \sum_{0 \le j < T} (u_{ij} - \bar{u}^*)^2. \qquad (20)$$

$$\sigma_{uu^*} = \frac{1}{S \times T - 1} \sum_{0 \le i < S} \sum_{0 \le j < T} (u^*_{ij} - \bar{u}^*)(u_{ij} - \bar{u}) \qquad (21)$$

The average angular error is:

$$\bar{\theta}_{Error} = \frac{\sum_{i=1}^{N} |\overset{\square}{\theta}_i - \theta_i|}{N}, \qquad (22)$$

where $\overset{\square}{\theta}_i$ is the projection angle after calibration, and $\theta_i$ is the original projection angle. The parametric error is:

$$P_{Error} = |P - P_{On}|, \qquad (23)$$

where P is the parameter vector after calibration, and $P_{On}$ is the real parameter vector. The average object x- and y-coordinate offsets are:

$$\bar{x} = \frac{\sum_{i=1}^{N} |x_i - \tilde{x}_i|}{N}, \qquad (24)$$

$$\bar{y} = \frac{\sum_{i=1}^{N} |y_i - \tilde{y}_i|}{N}, \qquad (25)$$

where $x_i$ and $y_i$ are the original object x- and y-coordinate offsets, while $\tilde{x}_i$ and $\tilde{y}_i$ are the calibrated offsets, respectively.

In many embodiments, image reconstruction can be performed using the Ordered Subset Simultaneous Algebraic Reconstruction Technique (OS-SART). OS-SART is discussed in Wang et al. (Ordered-subset simultaneous algebraic reconstruction techniques, *Journal of X-ray Science and Technology*, 12(3) (2004), 169-177), which is hereby incorporated herein by reference in its entirety. In addition, Total Variation (TV) regularization can be used. TV is discussed in detail in Sidky et al. (Accurate image reconstruction from few-views and limited-angle data in divergent beam CT, *Journal of X-ray Science and Technology*, 14(2) (2006), 119-139), which is hereby incorporated herein by reference in its entirety.

In an embodiment, a CT system can include a radiation source (e.g., an X-ray source), a detector for detecting radiation (e.g., X-rays) from the radiation source, and a computer system and/or one or more computer readable media having computer-executable instructions (stored thereon) for performing a method as disclosed herein. For example, the computer-executable instructions can be for performing an iterative reconstruction algorithm and/or a geometric calibration for CT (e.g., X-ray CT).

Embodiments of the subject invention provide calibration of a CT system (e.g., an X-ray CT system, such as a two-dimensional X-ray CT system) of view-wise random geometric parameters. LLE can be used as an important step to estimate geometric parameters subject to inherent low-dimensional consistency, and this has been demonstrated to provide significant improvements (see the Examples). LLE can find the K nearest re-projected projection vectors with the corresponding sampled parameters and update geometric parameters based on the linear combination of sampled parameters with weighting coefficients calculated via LLE.

Unified image reconstruction and parameter estimation schemes disclosed herein can include iteratively updating the projection matrix and an underlying image by re-projection and LLE. This can be applied to CT system (e.g., X-ray CT system) calibration and rigid patient motion compensation. Though fan-beam geometry and rigid patient motion have been specifically discussed, this is for exemplary purposes only and should be construed as limiting. Embodiments of the subject invention can be used with other types of geometry (e.g., cone-beam geometry) and other types of movement (e.g., non-rigid patient motion).

Embodiments of the subject invention can use one or more iterative reconstruction algorithms (e.g., based on Total Variation) to reconstruct better images, and then use the reconstructed images to adjust inaccurate parameters with LLE method. Adjusted parameters can then be used to reconstruct new images, and then the new images can be used to adjust inaccurate parameters. This iterative process can be repeated (e.g., until one or more threshold values of one or more characteristics (e.g., UQI) is met) to obtain desirable parameters. This can lead to automatic system calibration for CT (e.g., X-ray CT), thereby allowing for financial savings by eliminating the need for certain expensive machinery. Inaccurate parameters can be adjusted mathematically, allowing reconstruction of CT images with better quality.

For (X-ray) CT, geometric calibration and patient motion compensation (e.g., rigid patient motion compensation) are inter-related issues for optimization of image reconstruction quality. Non-calibrated system geometry and patient movement during a CT scan will result in streak-like blurring and other artifacts in reconstructed images. The LLE approach disclosed herein addresses this challenge and can be performed under a rigid two-dimensional object assumption, thereby addressing challenges of geometric calibration and patient motion compensation in a more general way than any related art methods. Projections can be linearly represented by up-sampled neighbors via LLE, and CT system parameters can be iteratively estimated from projection data.

Methods and systems of the subject invention can be used in current CT systems, especially in low-cost CT systems having inaccurate machinery (and therefore in need of parameter adjustment). In related art CT systems, large amounts of money are spent on accurate machinery, leading to high-cost CT systems that may not be affordable to small hospitals and clinics. The mathematical parameter adjustment methods and systems of the subject invention, which don't require high-cost, high-accuracy machinery, can adjust parameters only with computer equipment (e.g., a processing device such as a computer and/or one or more computer readable media). Methods and systems of the subject invention are also valuable for CT manufacturers by allowing reduction in the production cost of the CT system, which could lead to the development of a low-cost system and/or a portable CT system that could increase overall CT system sales.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A method of reconstructing a computed tomography (CT) image, the method comprising:

i) obtaining an initial CT image;

ii) performing a reconstruction algorithm on the initial CT image to obtain a reconstructed image of the initial CT image;

iii) using the reconstructed image to adjust one or more parameters associated with the image (e.g., the initial CT image or the previous reconstructed image) or the CT system from which the initial CT image was obtained;

iv) using the adjusted one or more parameters to perform the reconstruction algorithm on the reconstructed image to obtain an updated reconstructed image; and v) repeating steps iii)-iv) (using the most-recently updated reconstructed image in each repeated step iii), and updating the same parameter(s) in each repeated step iii)) until a threshold value of a predetermined characteristic is met.

Embodiment 2

The method according to embodiment 1, wherein the reconstruction algorithm is based on Total Variation (TV).

Embodiment 3

The method according to any of embodiments 1-2, wherein using the reconstructed image to adjust one or more parameters associated with the image comprises is done using a Locally Linear Embedding (LLE) method on each of the one or more parameters.

Embodiment 4

The method according to embodiment 3, wherein the LLE method includes:

step 1) finding the K nearest neighbors for each high-dimensional point in terms of the Euclidean distance;

step 2) representing each point linearly with its neighbors and calculating weight coefficients for its neighbors; and step 3) mapping high dimensional data with the weight coefficients to a low dimensional representation on an intrinsic manifold.

Embodiment 5

The method according to any of embodiments 3-4, wherein the LLE method includes:

finding the K nearest neighbors of a data vector $b_i$ in its dataset vectors $\tilde{b}_{ij}$ according to the Euclidean distance:

$$d_{ij} = \|b_i - \tilde{b}_{ij}\|_2^2.$$

Embodiment 6

The method according to any of embodiments 3-5, wherein the LLE method (further) includes:
with the K nearest vectors, representing the original data vector linearly with its neighboring vectors:

$$b_i = \sum_{k=1}^{K} w_{ik} \tilde{b}_{ik},$$

where $\tilde{b}_{ik}$ are the K nearest neighbors and $w_{ik}$ are respectively weight coefficients, and $$\sum_k w_{ik} = 1,$$

and the weight matrix can be solved by minimizing the following error:

$$\min \left\| b_i - \sum_k w_{ik} \tilde{b}_{ik} \right\|_2^2 \text{ s.t.} \sum_j w_{ik} = 1.$$

Embodiment 7

The method according to embodiment 6, wherein, using the constraint $$\sum_k w_{ik} = 1,$$

minimizing the error is equivalent to solving the linear system:

$$\sum_k c_{jk} w_{ik} = 1,$$

where $C=(c_{jk})$ is the local covariance matrix calculated as:

$$C=(b_i-\tilde{b}_{ik})^T(b_i-\tilde{b}_{ik}).$$

Embodiment 8

The method according to any of embodiments 3-7, wherein the LLE method (further) includes, calculating, with the weight coefficients $W=(w_{ik})$, the global internal coordinate $Y=(y_i)$ by solving the equation:

$$\min_Y \sum_i \left\| y_i - \sum_k w_{ik} y_k \right\|_2^2.$$

Embodiment 9

The method according to embodiment 8, wherein the solution of the equation that can be solved to calculate $Y=(y_i)$ is given by the bottom d+1 eigenvectors of the generalized eigenvalue problem:

$$MY=\lambda Y,$$

where $\lambda$ is the eigenvalue, and $M=(I-W)^T(I-W)$.

Embodiment 10

The method according to any of embodiments 3-9, wherein the number of nearest neighbors used in the LLE method is K=2.

Embodiment 11

The method according to any of embodiments 3-9, wherein the number of nearest neighbors used in the LLE method is at least 2.

Embodiment 12

The method according to any of embodiments 1-11, wherein the predetermined characteristic, of which a threshold value must be met to stop repeating steps iii)-iv) is universal quality index (UQI).

Embodiment 13

The method according to embodiment 12, wherein the threshold value is 0.6.

Embodiment 14

The method according to embodiment 12, wherein the threshold value is at least 0.6.

Embodiment 15

The method according to embodiment 12, wherein the threshold value is 0.7.

Embodiment 16

The method according to embodiment 12, wherein the threshold value is at least 0.7.

Embodiment 17

The method according to embodiment 12, wherein the threshold value is 0.8.

Embodiment 18

The method according to embodiment 12, wherein the threshold value is at least 0.8.

Embodiment 19

The method according to embodiment 12, wherein the threshold value is 0.9.

Embodiment 20

The method according to embodiment 12, wherein the threshold value is at least 0.9.

Embodiment 21

The method according to embodiment 12, wherein the threshold value is 0.95.

Embodiment 22

The method according to embodiment 12, wherein the threshold value is at least 0.95.

Embodiment 23

The method according to embodiment 12, wherein the threshold value is 0.5.

Embodiment 24

The method according to embodiment 12, wherein the threshold value is at least 0.5.

Embodiment 25

The method according to any of embodiments 1-24, wherein the one or more parameters includes at least one of projection angle, source-to-object distance (SOD), object-to-detector distance (ODD), detector offset, detector tilt angle, object x-coordinate offset, object y-coordinate offset, and projection angular error.

Embodiment 26

The method according to any of embodiments 1-24, wherein the one or more parameters includes at least two of projection angle, SOD, ODD, detector offset, detector tilt angle, object x-coordinate offset, object y-coordinate offset, and projection angular error.

Embodiment 27

The method according to any of embodiments 1-24, wherein the one or more parameters includes at least three of projection angle, SOD, ODD, detector offset, detector tilt angle, object x-coordinate offset, object y-coordinate offset, and projection angular error.

Embodiment 28

The method according to any of embodiments 1-24, wherein the one or more parameters includes at least four of projection angle, SOD, ODD, detector offset, detector tilt angle, object x-coordinate offset, object y-coordinate offset, and projection angular error.

Embodiment 29

The method according to any of embodiments 1-24, wherein the one or more parameters includes projection angle, SOD, ODD, detector offset, and detector tilt angle.

Embodiment 30

The method according to any of embodiments 1-24, wherein the one or more parameters includes object x-coordinate offset, object y-coordinate offset, and projection angular error.

Embodiment 31

The method according to any of embodiments 3-30, wherein the LLE method includes solving the following linear system of equations:

$$Au=b_i,$$

where $u=(u_1, u_2, \ldots, u_J)$ is an image represented as a J dimensional vector, J is the number of pixels, $b_i=(b_1, b_2, \ldots, b_L)$ is data, L is the number of vector elements, and $A=(a_{jk})$ is a projection matrix related to the one or more (geometric) parameters.

Embodiment 32

The method according to embodiment 31, wherein performing the reconstruction algorithm comprises calculating a projection matrix, which is affected by the one or more (geometric) parameters:

$$A=A(P),$$

where P is an estimated parameter vector, which includes the one or more parameters.

Embodiment 33

The method according to embodiment 32, wherein the projections of the projection matrix are calculated using a distance-driven method.

Embodiment 34

The method according to any of embodiments 32-33, wherein using the reconstructed image to adjust one or more parameters comprises minimizing the mean squared error between the projection data and re-projected projection data, which can be formulated as:

$$P=\arg\min \|b_i - \tilde{b}_{ij}\|_2^2 \text{ s.t } A(P)u=b_i,$$

where $b_i$ is the projection vector obtained from the measurement along different projection views, $\tilde{b}_{ij}$ is the corresponding re-projected projection vector from a reconstructed image with sampled parameters, and P is the updated vector of parameters.

Embodiment 35

The method according to embodiment 34, wherein the re-projected projection vector can be calculated by the equations provide in embodiments 31 and 32 within a densely sampled parametric range:

$$\tilde{P}_j=(p_{j1}, p_{j2}, \ldots, p_{jn}).$$

Embodiment 36

The method according to embodiment 35 wherein a true parameter vector is close to neighboring sampled parameter vectors, and the measured projection vector can be linearly expressed by the K nearest re-projected projection vectors associated with the sampled parameter vectors, such that:

$$b_i = \sum_{k=1}^{K} w_{ik} \tilde{b}_{ik},$$

and $$P = \sum_{k=1}^{K} w_{ik} \tilde{P}_k,$$

where $\tilde{b}_{ik}$ are the K nearest re-projection vectors associated with the corresponding K vectors of parameters $\tilde{P}_k$, and $w_{ik}$ are weight coefficients.

Embodiment 37

The method according to any of embodiments 1-36, wherein obtaining the initial CT image comprises obtaining an initial parameter vector including initial value(s) for the one or more parameters associated with the image (e.g., the initial CT image or the previous reconstructed image) or the CT system from which the initial CT image was obtained.

Embodiment 38

The method according to embodiment 37, performing the reconstruction algorithm comprises updating the parameter vector with updated value(s) of the one or more parameters based on the (most recently) reconstructed image.

Embodiment 39

The method according to any of embodiments 1-38, wherein the reconstruction algorithm comprises using an Ordered Subset Simultaneous Algebraic Reconstruction Technique (OS-SART).

Embodiment 40

The method according to any of embodiments 1-39, wherein the reconstruction algorithm comprises using TV for regularization.

Embodiment 41

The method according to any of embodiments 1-40, wherein step ii) is performed by a processor.

Embodiment 42

The method according to any of embodiments 1-41, wherein step iii) is performed by a processor.

Embodiment 43

The method according to any of embodiments 1-42, wherein step iv) is performed by a processor.

Embodiment 44

The method according to any of embodiments 1-43, wherein step v) is performed by a processor.

Embodiment 45

A computer readable medium having computer-executable instructions (stored thereon) for performing the method according to any of embodiments 1-44.

Embodiment 46

A CT system, comprising:
a radiation source (e.g., an X-ray source);
a detector for detecting radiation (e.g., X-rays) from the radiation source; and
a computer having the computer readable medium according to embodiment 45.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 15:
FIG. 15 shows an image of an abdomen phantom from a real CT scan.

The LLE-based calibration approach was evaluated using an abdomen image phantom from a clinic, shown in FIG. 15. The size of the abdomen phantom was 512×512. With this phantom, projection data with angular and other geometric errors were generated. Then, the algorithm described herein was applied to the projection data with geometric parameter errors. The algorithm was tested in a rigid patient motion problem. The computational environment was MatLab 2010a on a computer with an Intel Core 2 Duo E7600 CPU @3.06 GHz, 4.00 GB RAM, and a 64-bit OS.

To evaluate reconstructed images, UQI was used. Also, geometric calibration results were quantified with the average angular error $\bar{\theta}_{error}$, parametric error $P_{Error}$, and average object coordinate offsets $\bar{x}$ and $\bar{y}$.

The image reconstruction process was performed using OS-SART with TV regularization. As the reconstruction and calibration iteration stop criteria, satisfactory UQI values were monitored for in both the image and projection domains.

The utility of the calibration approach was evaluated for reducing projection angular and other geometric errors. The number of projection angles N=360. The projection angles were randomly perturbed as follows:

$$\theta_i = 360 \times (i-1)/N + \delta_i, \ i=1,2,\ldots,N. \quad (26)$$

The other parameters used are shown in Table 1, including the real values, initial values, and final estimates. The length of the detector array was 80 cm. With the geometric parameters, projection data were generated with Poisson noise, assuming that the number of incoming X-ray photons was $10^5$.

To calibrate the parameters efficiently, first the geometric parameters were calibrated one by one rather than all the parameters together being calibrated together. The calibration process proceeded in the following sequence: detector offset; SOD; ODD; detector tilt; and projection angle. The angular sampling steps for each parameter were 0.04 cm, 0.1 cm, 0.1 cm, 0.01°, and 0.02° respectively. The sampling ranges were [0 cm, 0.4 cm], [46 cm, 54 cm], [46 cm, 54 cm], [0°, 2°], and [−1°, 1°] respectively. The number of nearest neighbors was 2. The UQI threshold for stopping was 0.9 for reconstruction and 0.6 for calibration.

Figure 16A:
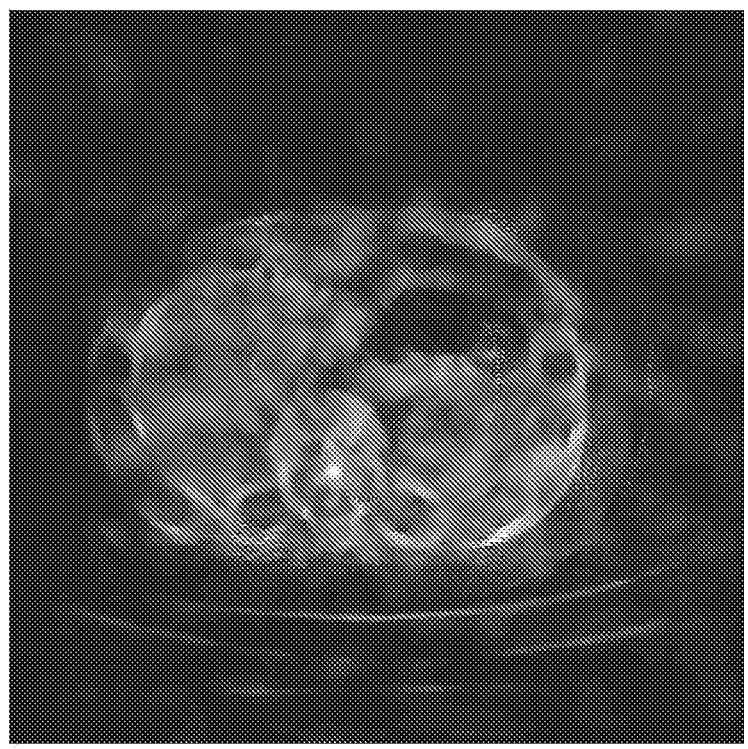
FIG. 16A shows a reconstructed image of the abdomen phantom shown in FIG. 15 before any compensation.
Figure 16B:
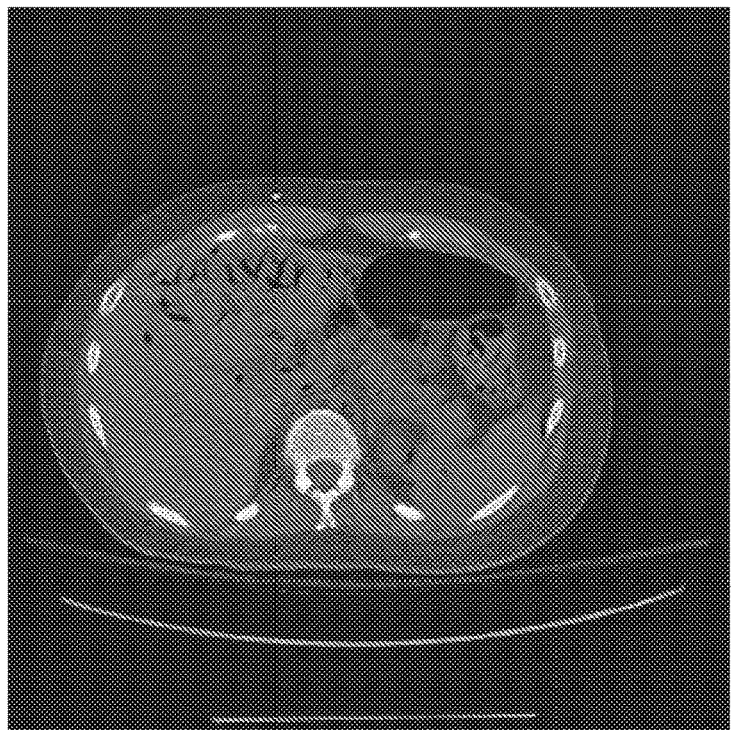
FIG. 16B shows a reconstructed image of the abdomen phantom shown in FIG. 15 after one iteration of a calibration according to an embodiment of the subject invention.
Figure 16C:
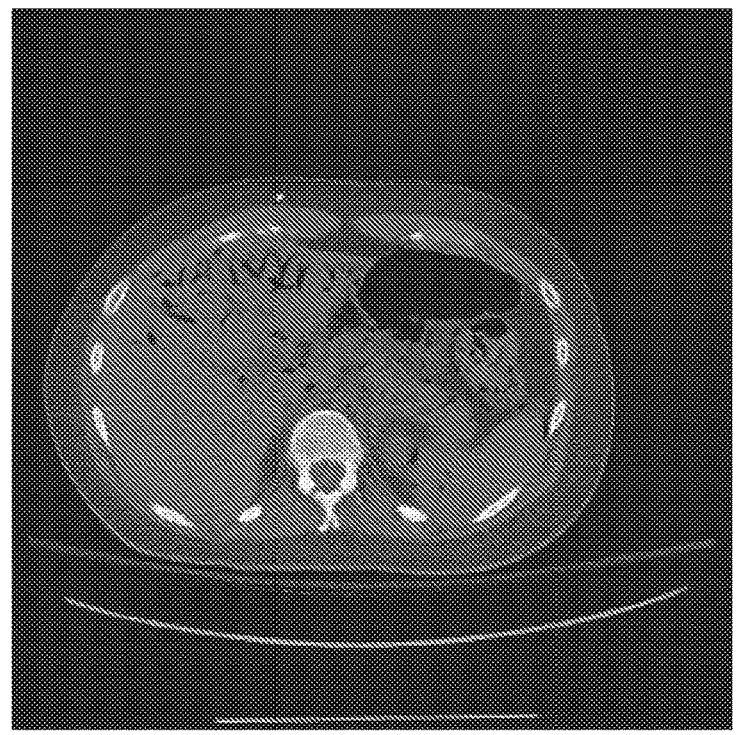
FIG. 16C shows a reconstructed image of the abdomen phantom shown in FIG. 15 after two iterations of a calibration according to an embodiment of the subject invention.
Figure 16D:
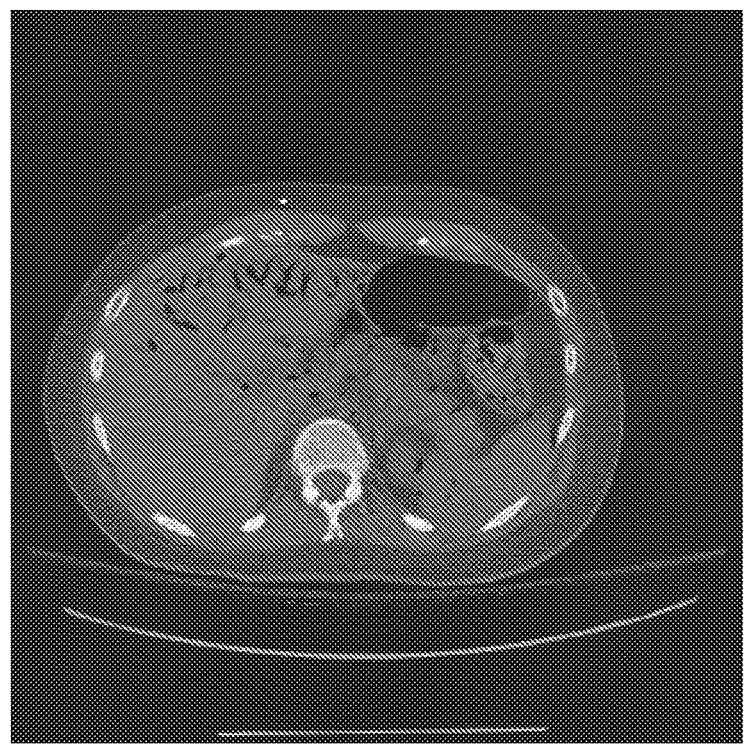
FIG. 16D shows a reconstructed image of the abdomen phantom shown in FIG. 15 after four iterations of a calibration according to an embodiment of the subject invention.

FIG. 16A shows the reconstructed image of FIG. 15 before any compensation; FIGS. 16B-16D show the reconstructed image of FIG. 15 after one iteration, two iterations, and four iterations, respectively, of the geometric calibration. The calibrated parameters are shown in Table 1.

TABLE 1

Real geometric, initial, and calibrated parameters.

| Parameter | Detector offset (cm) | Detector tilt (°) | Source object distance (cm) | Object detector distance (cm) | Average angle error (°) |
|---|---|---|---|---|---|
| Real | 2 | 1 | 50 | 50 | |
| Initial | 0 | 0 | 46 | 46 | 0.5015 |
| Calibrated | 2.0112 | 1.0918 | 52.7156 | 46.4990 | 0.1257 |

Figure 17A:
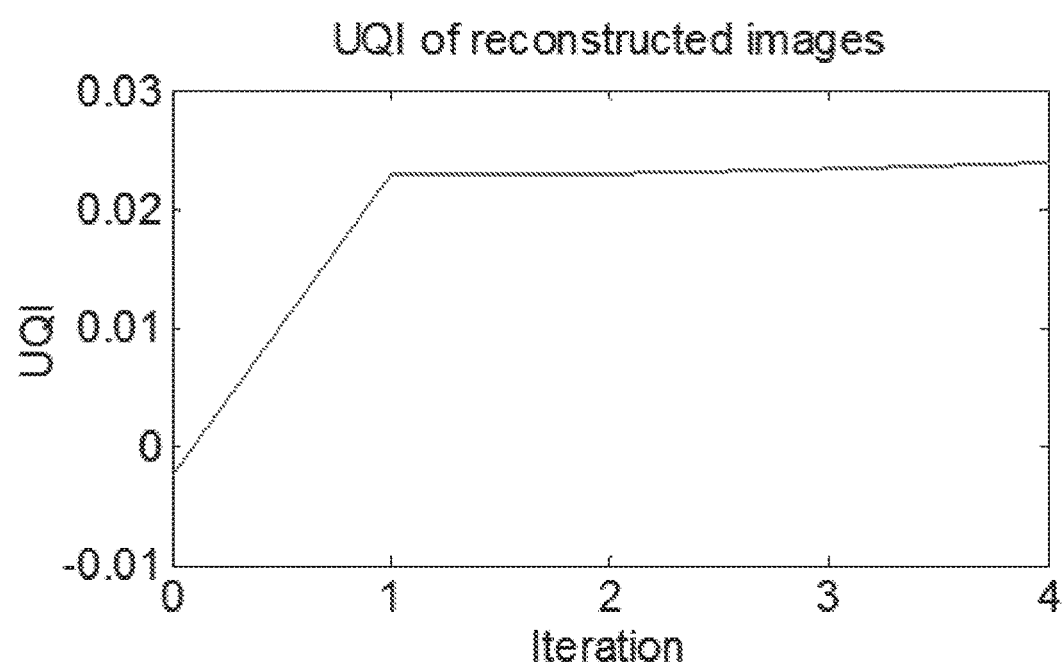
FIG. 17A shows a plot of universal quality index (UQI) of reconstructed images versus iteration of a calibration according to an embodiment of the subject invention.
Figure 17B:
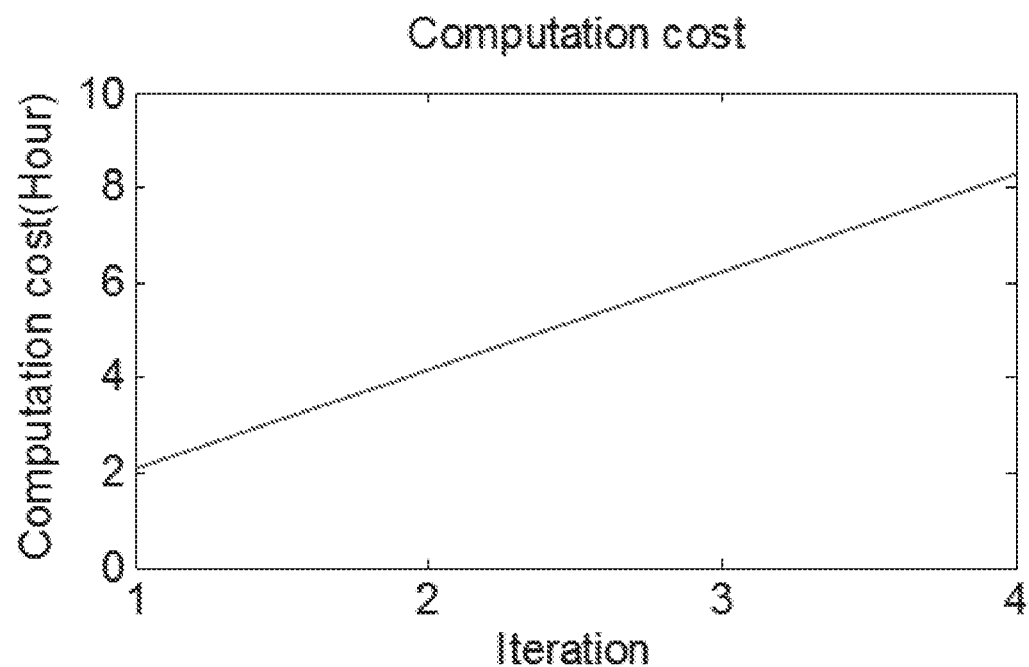
FIG. 17B shows a plot of computation cost (in hours) of reconstructed images versus iteration of a calibration according to an embodiment of the subject invention.
Figure 17C:
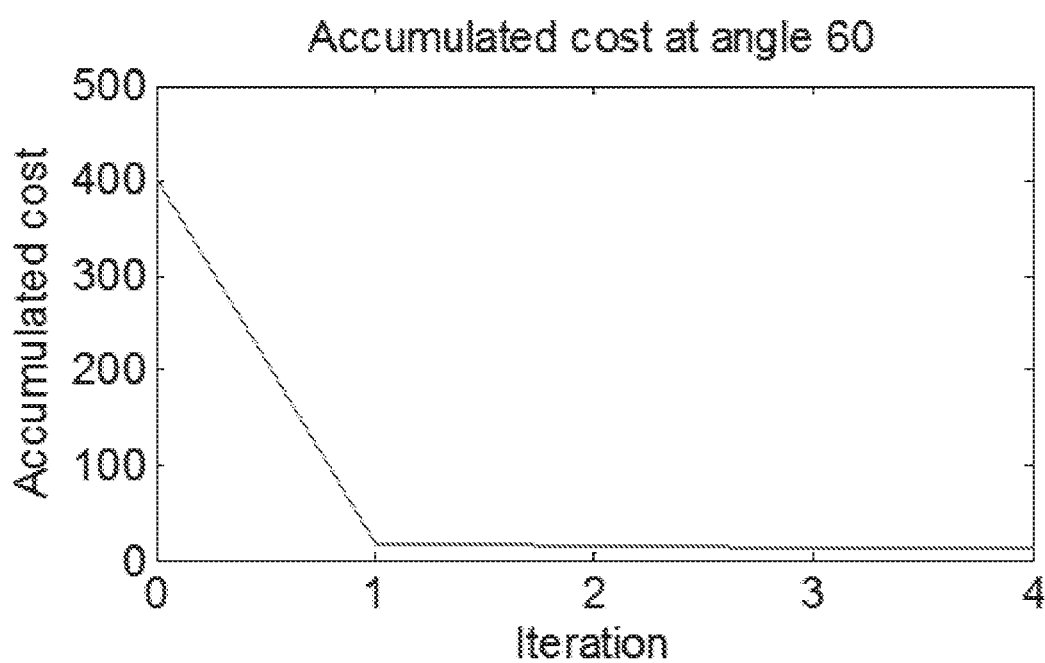
FIG. 17C shows a plot of accumulated cost at angle 60 of reconstructed images versus iteration of a calibration according to an embodiment of the subject invention.
Figure 18A:
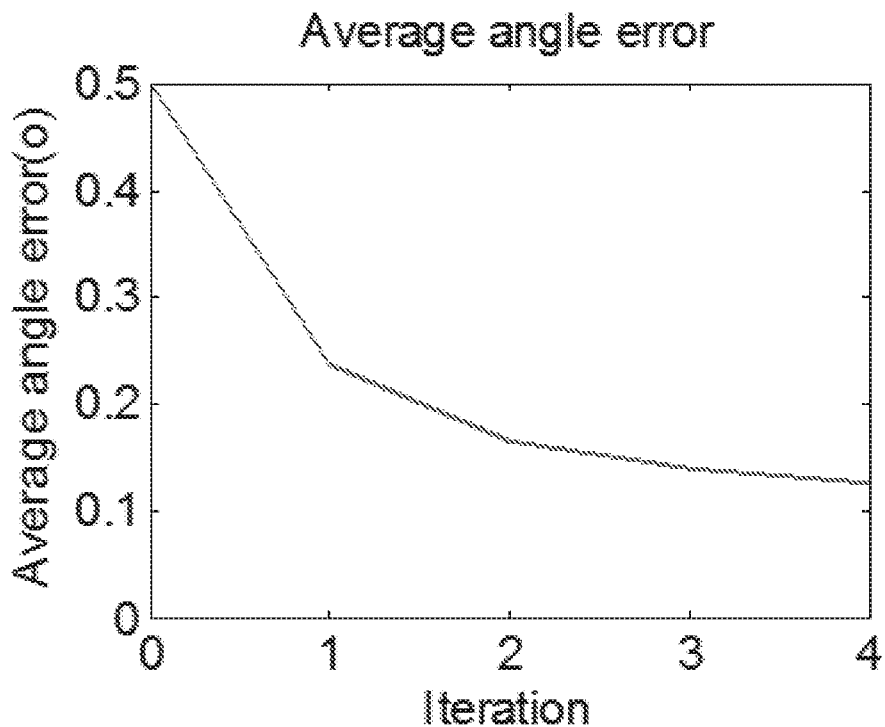
FIG. 18A shows a plot of average angle error (in degrees) of reconstructed images versus iteration of a calibration according to an embodiment of the subject invention.
Figure 18B:
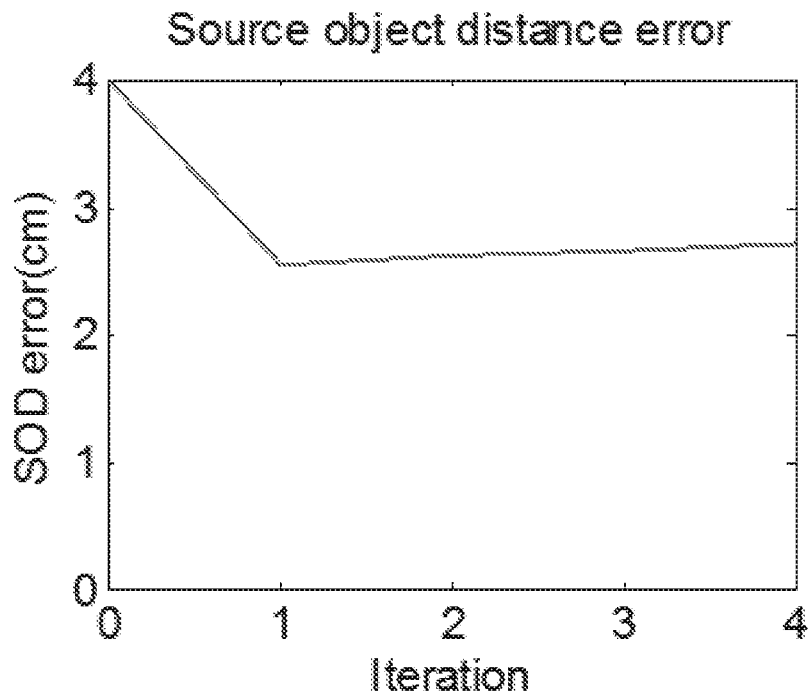
FIG. 18B shows a plot of source-object distance (SOD) (in cm) of reconstructed images versus iteration of a calibration according to an embodiment of the subject invention.
Figure 18C:
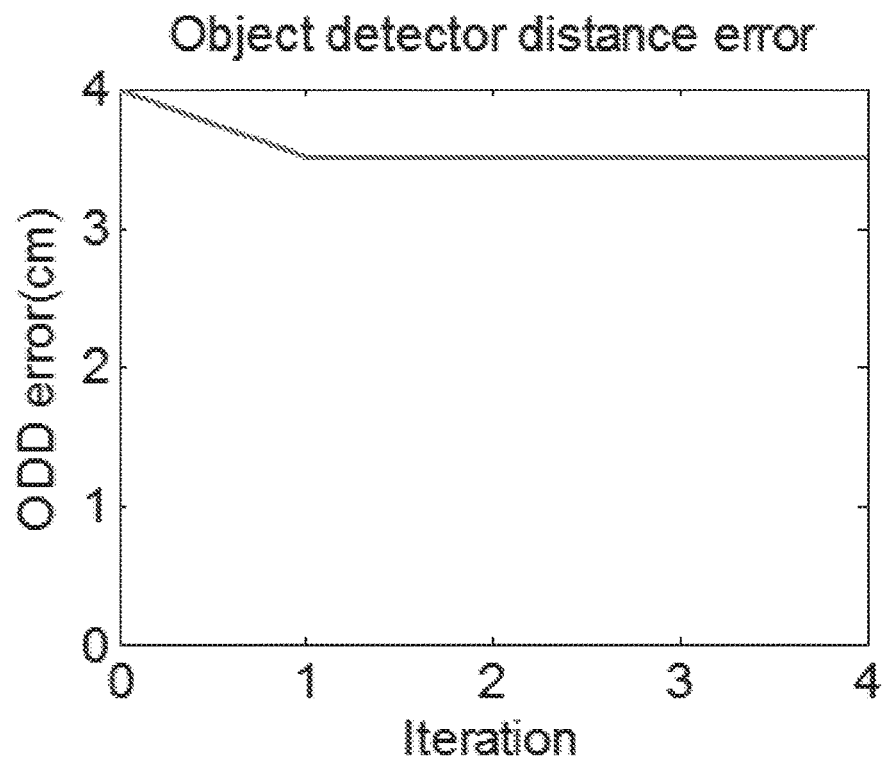
FIG. 18C shows a plot of object-detector distance (ODD) (in cm) of reconstructed images versus iteration of a calibration according to an embodiment of the subject invention.
Figure 18D:
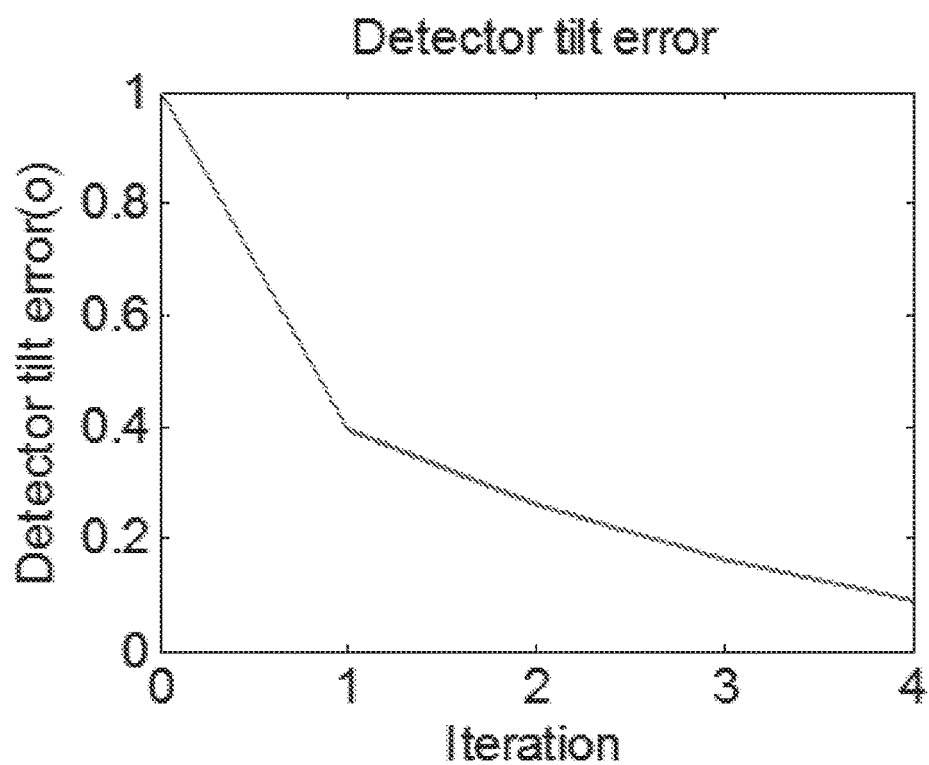
FIG. 18D shows a plot of detector tilt error (in degrees) of reconstructed images versus iteration of a calibration according to an embodiment of the subject invention.
Figure 18E:
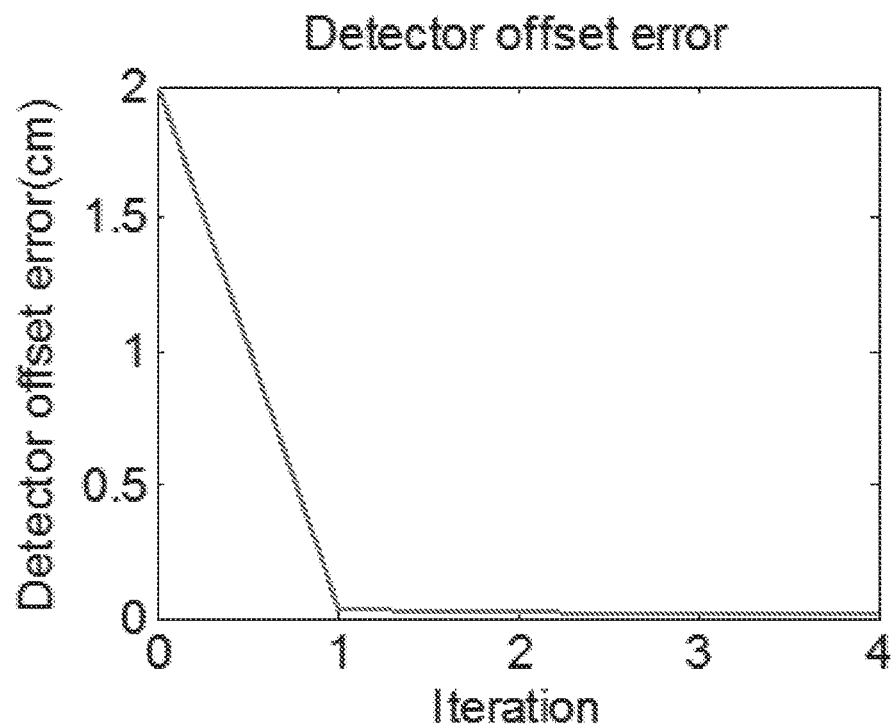
FIG. 18E shows a plot of detector offset error (in cm) of reconstructed images versus iteration of a calibration according to an embodiment of the subject invention.
Figure 19A:
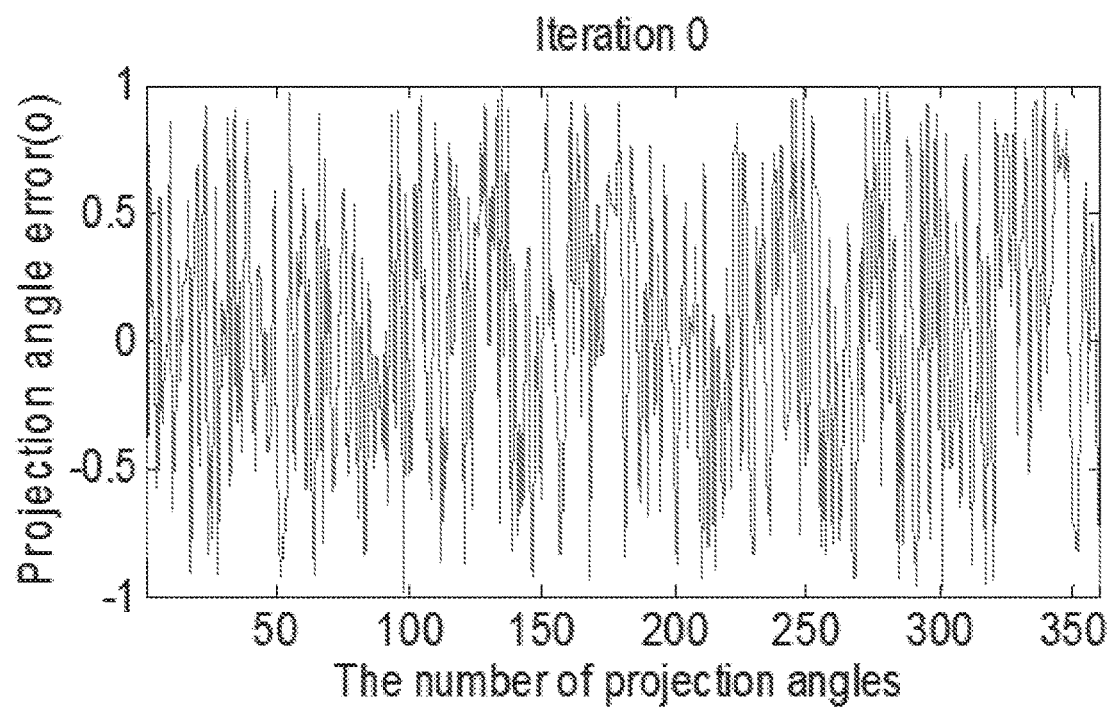
FIG. 19A shows a plot of projection angle error (in degrees) versus number of projection angles at "iteration 0" of a calibration (i.e., before calibration has begun).
Figure 19B:
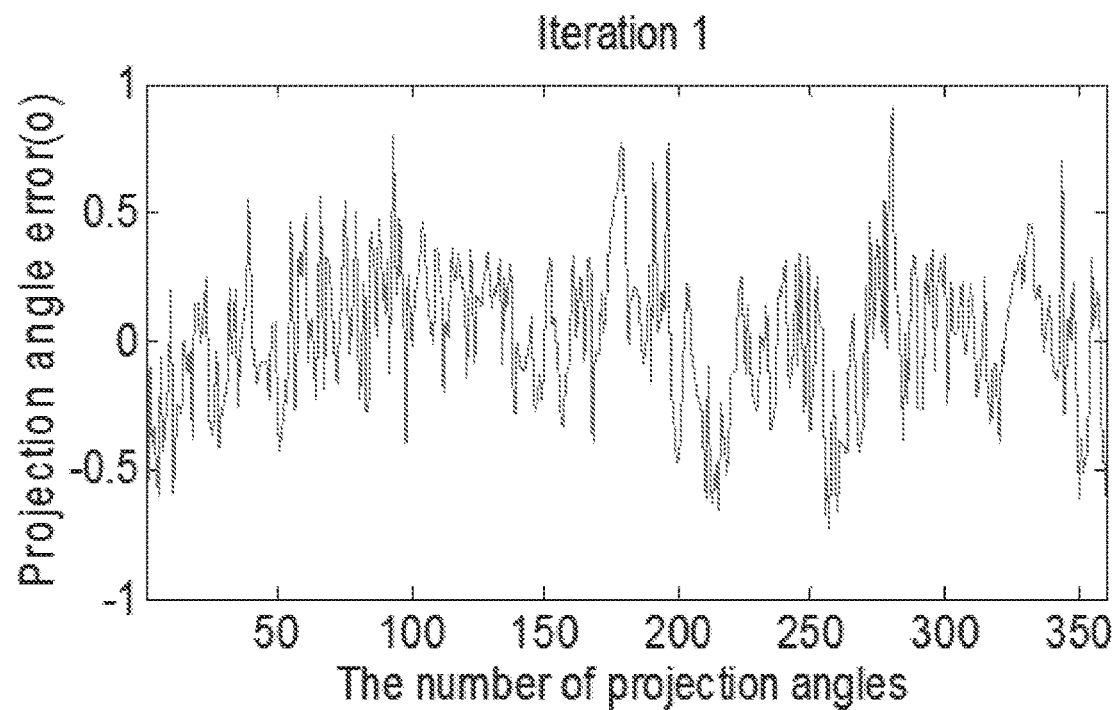
FIG. 19B shows a plot of projection angle error (in degrees) versus number of projection angles after one iteration of a calibration according to an embodiment of the subject invention.
Figure 19C:
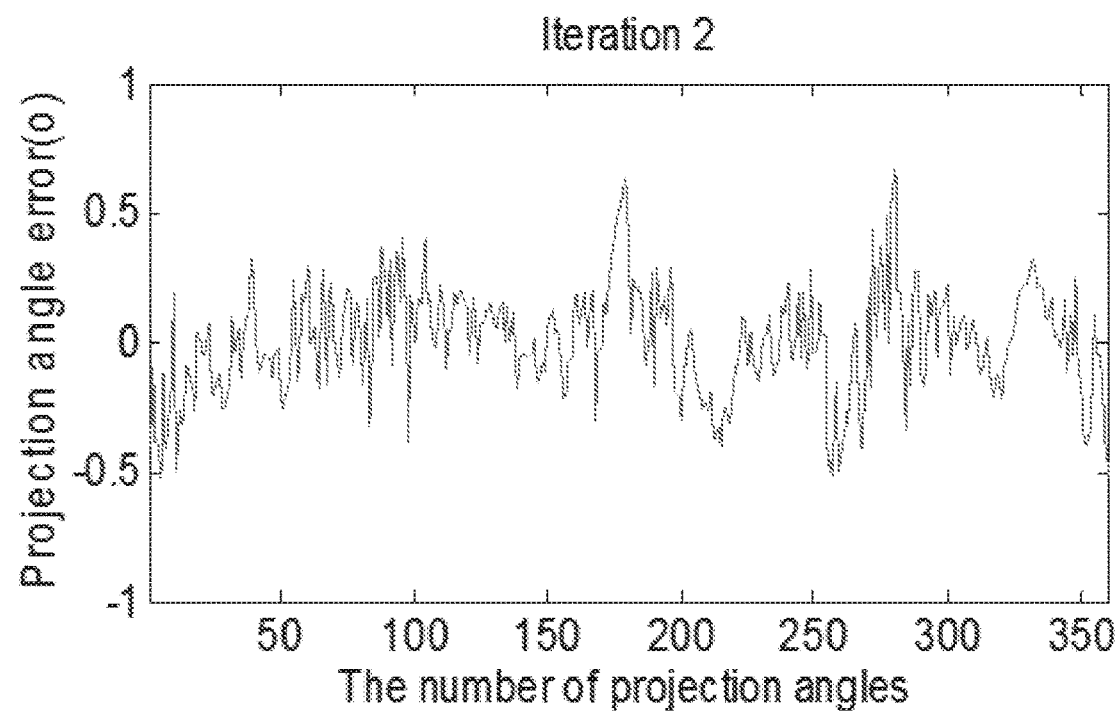
FIG. 19C shows a plot of projection angle error (in degrees) versus number of projection angles after two iterations of a calibration according to an embodiment of the subject invention.
Figure 19D:
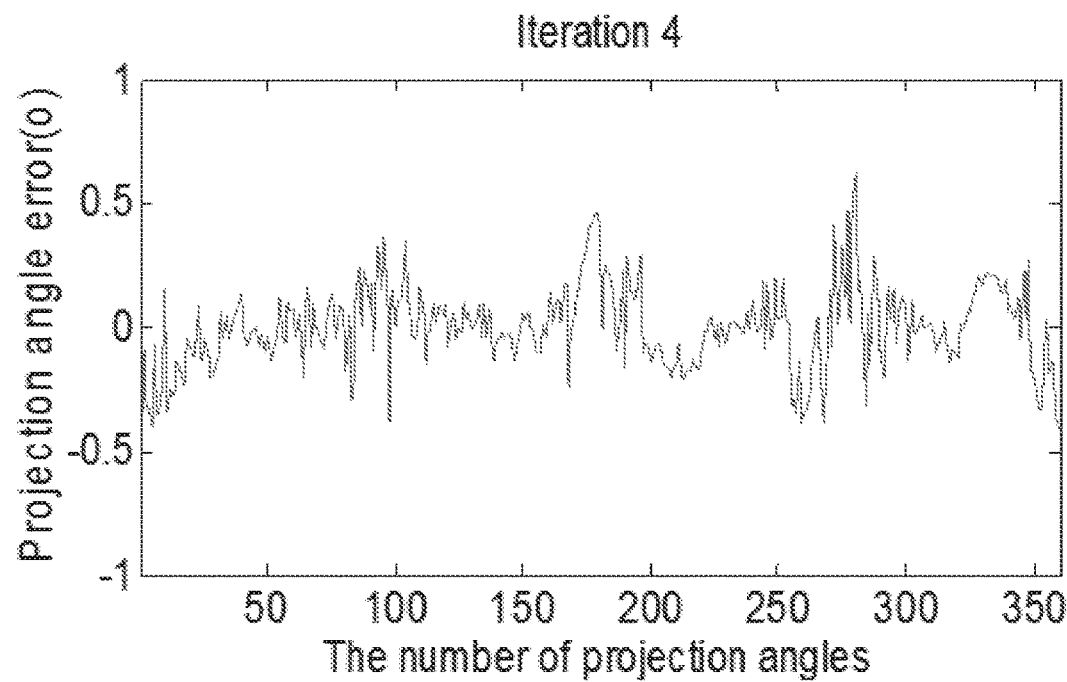
FIG. 19D shows a plot of projection angle error (in degrees) versus number of projection angles after four iterations of a calibration according to an embodiment of the subject invention.

FIG. 17A shows a plot of UQI of the reconstructed images versus iteration of the calibration; FIG. 17B shows a plot of computation cost (in hours) of the reconstructed images versus iteration of the calibration; and FIG. 17C shows a plot of accumulated cost at angle 60° of the reconstructed images versus iteration of the calibration. FIG. 18A shows a plot of average angle error (in degrees) of the reconstructed images versus iteration of the calibration; FIG. 18B shows a plot of SOD (in cm) of the reconstructed images versus iteration of the calibration; FIG. 18C shows a plot of ODD (in cm) of the reconstructed images versus iteration of the calibration; FIG. 18D shows a plot of detector tilt error (in degrees) of the reconstructed images versus iteration of the calibration; and FIG. 18E shows a plot of detector offset error (in cm) of the reconstructed images versus iteration of the calibration. FIG. 19A shows a plot of projection angle error (in degrees) versus number of projection angles at "iteration 0" of the calibration (i.e., before calibration has begun); FIG. 19B shows a plot of projection angle error (in degrees) versus number of projection angles after one iteration of the calibration; FIG. 19C shows a plot of projection angle error (in degrees) versus number of projection angles after two iterations of the calibration; and FIG. 19D shows a plot of projection angle error (in degrees) versus number of projection angles after four iterations of the calibration.

Referring to FIGS. 17A-17C, 18A-18E, and 19A-19D, and to Table 1, it can be seen that all parameters and characteristics of the reconstructed image improved significantly with the calibration process. For many parameters, only a small number of iterations was needed to see drastic improvement.

Example 2

Figure 20:
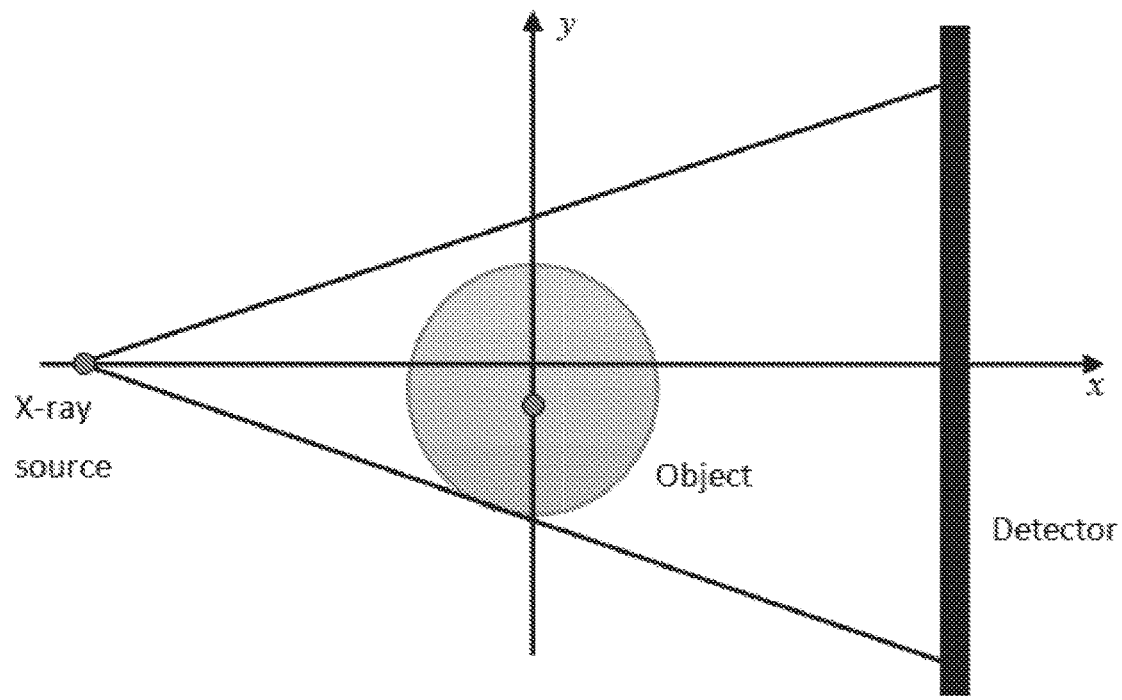
FIG. 20 shows a schematic view illustrating fan-beam X-ray CT geometry with a misaligned rotation stage.

The calibration algorithm discussed herein was applied in a case of real projection data with geometric parameter errors. The nominal SOD and ODD values were both 38 cm, the number of detector elements was 1024, and the length of the detector was 13.0048 cm. The number of projection angles was 900 in the angular range [0°, 360°]. An object was on the rotation stage while the rotation center was not on the line between the X-ray source and the detector center, as shown in FIG. 20, where the red spot (spot contained within the shaded circle) was the rotation center not on the system origin. Therefore, the algorithm was used to calibrate the rotation center offset. The sampling range was [−1 cm, 1 cm] with a sampling step of 0.05 cm. The number of nearest neighbors was 2. The UQI stopping threshold was 0.9 for reconstruction and 0.6 for calibration.

Figure 21A:
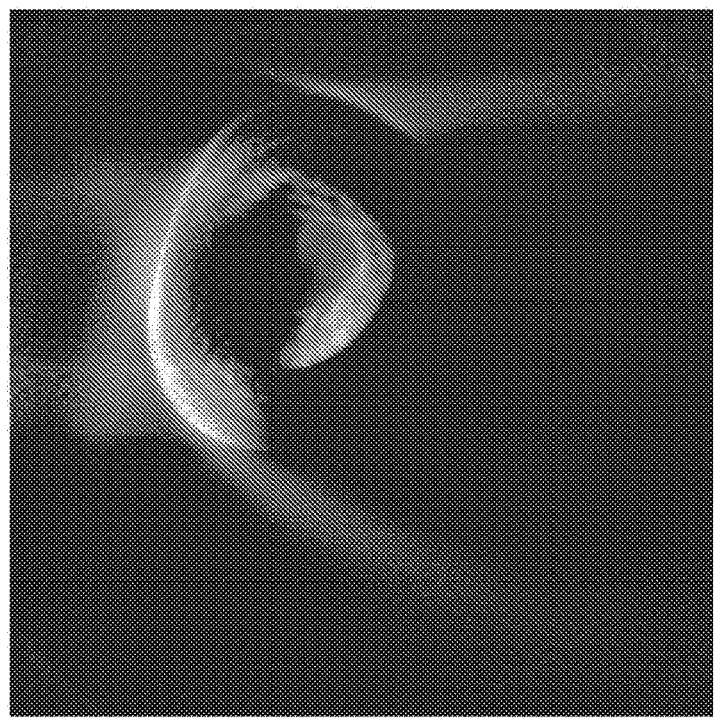
FIG. 21A shows a reconstructed image, before any compensation, of an object that was misaligned during CT scanning.
Figure 21B:
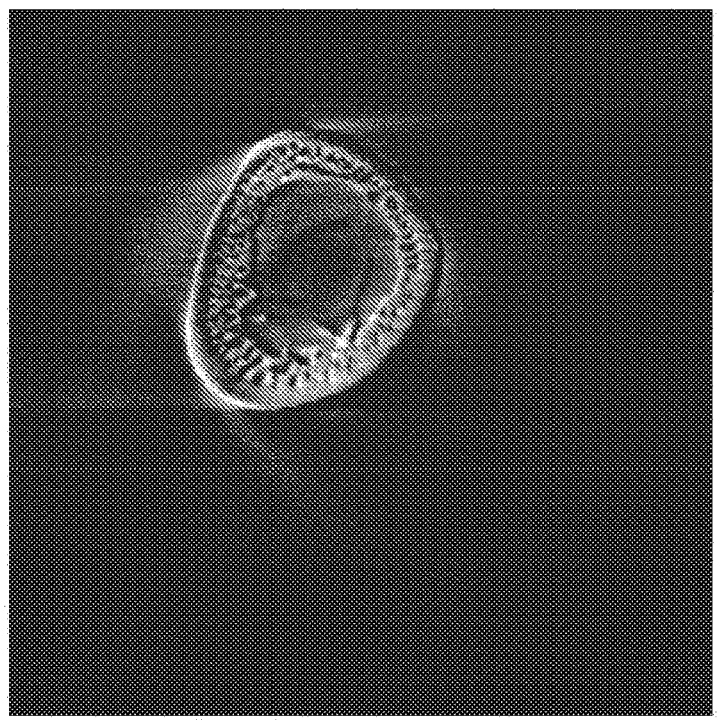
FIG. 21B shows a reconstructed image of the object depicted in FIG. 21A after one iteration of a calibration according to an embodiment of the subject invention.
Figure 21C:
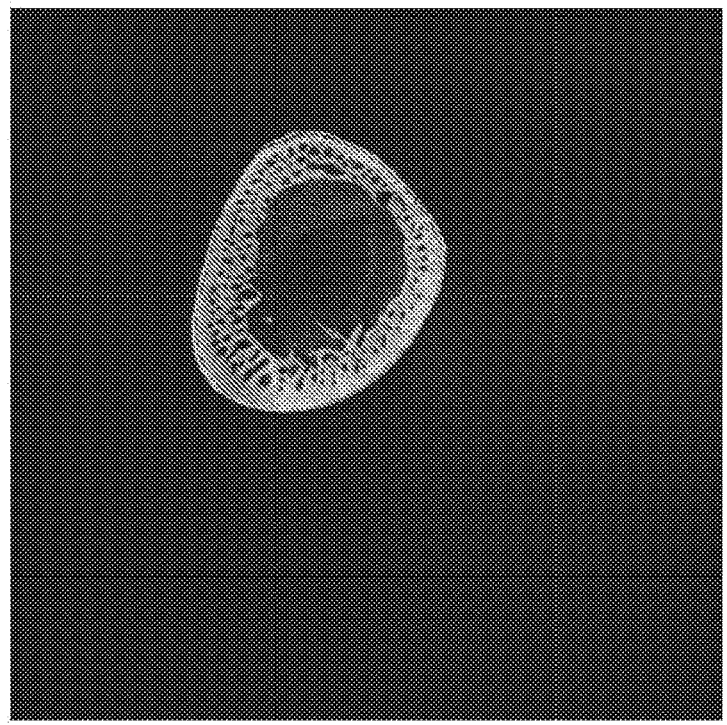
FIG. 21C shows a reconstructed image of the object depicted in FIG. 21A after two iterations of a calibration according to an embodiment of the subject invention.
Figure 21D:
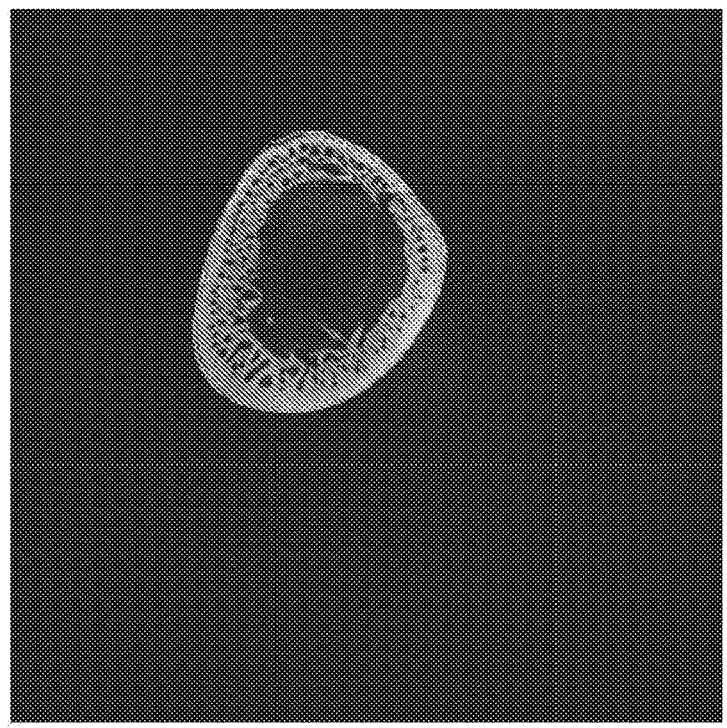
FIG. 21D shows a reconstructed image of the object depicted in FIG. 21A after five iterations of a calibration according to an embodiment of the subject invention.
Figure 22A:
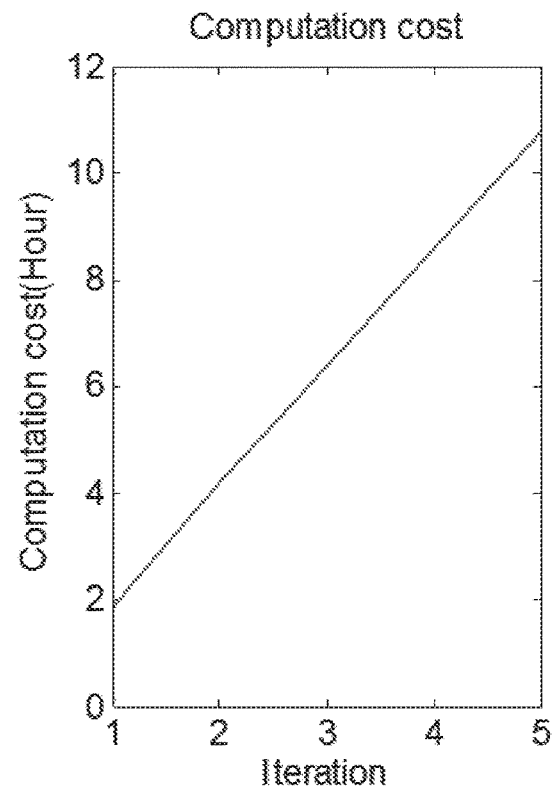
FIG. 22A shows a plot of computation cost (in hours) of reconstructed images versus iteration of a calibration according to an embodiment of the subject invention.
Figure 22B:
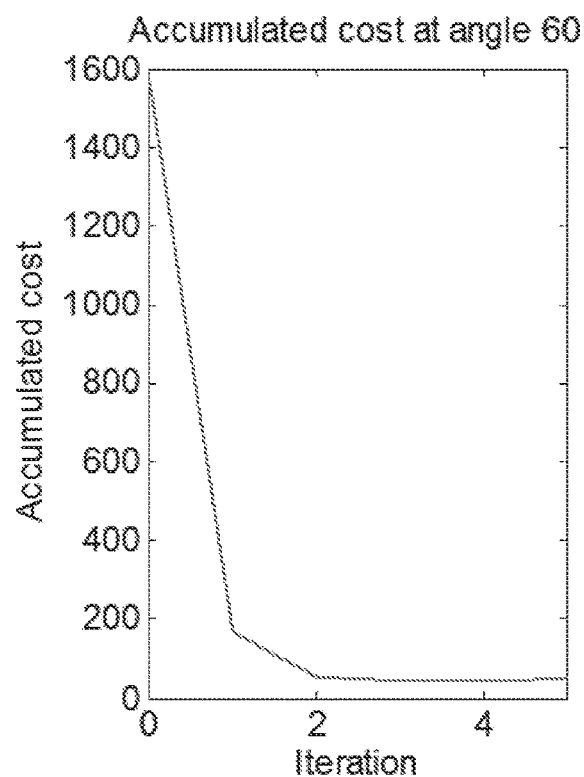
FIG. 22B shows a plot of accumulated cost at angle 60 of reconstructed images versus iteration of a calibration according to an embodiment of the subject invention.
Figure 22C:
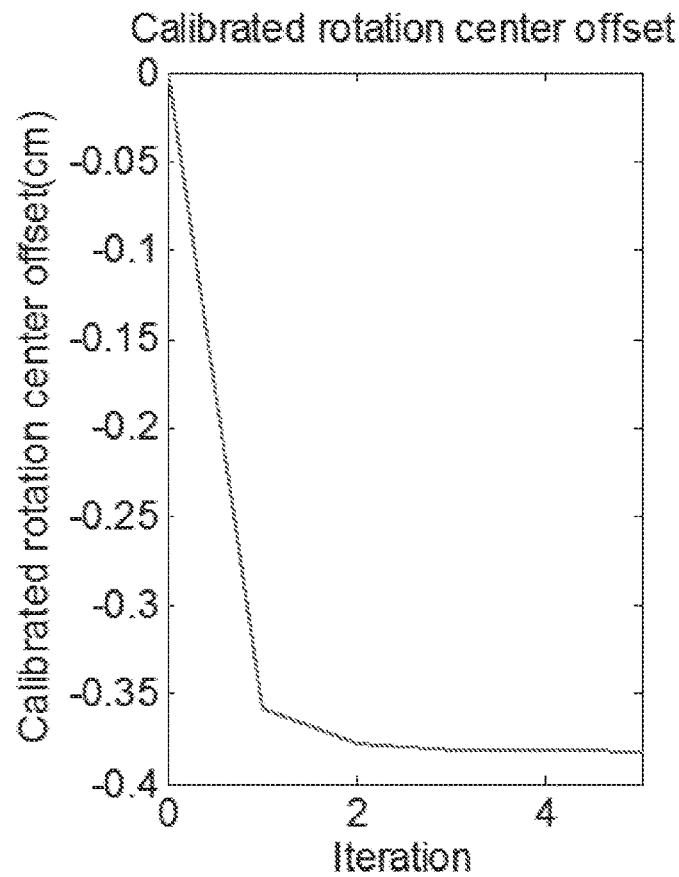
FIG. 22C shows a plot of calibrated rotation center offset (in cm) of reconstructed images versus iteration of a calibration according to an embodiment of the subject invention.

FIG. 21A shows the reconstructed image before any compensation. FIG. 21B shows the reconstructed image depicted in FIG. 21A after one iteration of the calibration; FIG. 21C shows the reconstructed image after two iterations; and FIG. 21D shows the reconstructed image after five iterations. In addition, FIG. 22A shows a plot of computation cost (in hours) of the reconstructed images versus iteration of the calibration; FIG. 22B shows a plot of accumulated cost at angle 60° of the reconstructed images versus iteration of the calibration; and FIG. 22C shows a plot of calibrated rotation center offset (in cm) of the reconstructed images versus iteration of the calibration. The calibrated rotation center offset was −0.3847 cm.

Referring to FIGS. 21A-21D and 22A-22C, it can be seen that all parameters and characteristics of the reconstructed image improved significantly with the calibration process. For many parameters, only a small number of iterations was needed to see drastic improvement.

Example 3

Calibration as discussed herein was tested for a situation involving rigid patient motion. As discussed, rigid patient motion can be represented as object x-coordinate offset error, object y-coordinate offset error, and projection angle error. Rigid patient motion calibration was simulated with an abdomen phantom. The number of projection angles and other parameters were the same as in Example 1. The object x-coordinate offset error and object y-coordinate offset error were all randomly selected within the range of [−1 cm, 1 cm], and the projection angle errors were randomly chosen within the range of [−1°, 1°].

The calibration was in the following sequence: object x-coordinate offset; object y-coordinate offset; and projection angle. The sampling rates for the parameters were 0.05 cm, 0.05 cm, and 0.1°, respectively. The sampling ranges were [−1 cm, 1 cm], [−1 cm, 1 cm], and [−1°, 1°], respectively. The number of nearest neighbors was K=2. The UQI stop value for reconstruction was 0.9 and for calibration was 0.8.

Figure 23A:
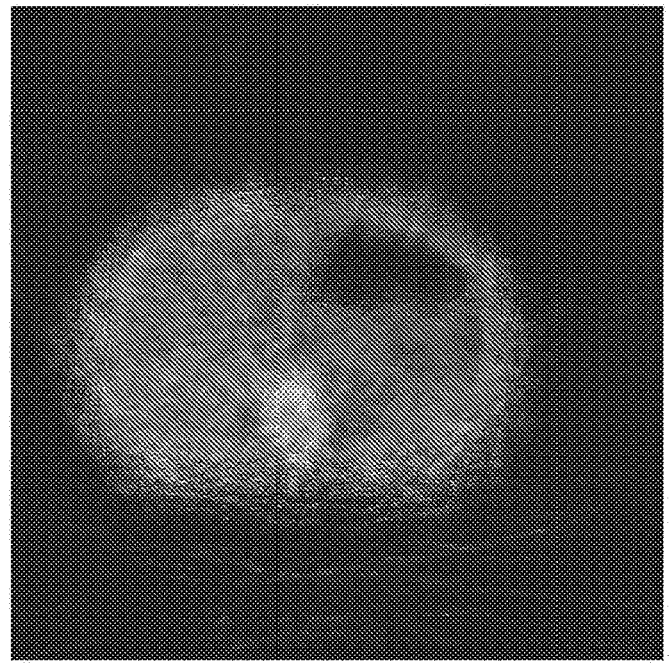
FIG. 23A shows a reconstructed image, before any compensation, of an object that was scanned using a CT scanner.
Figure 23B:
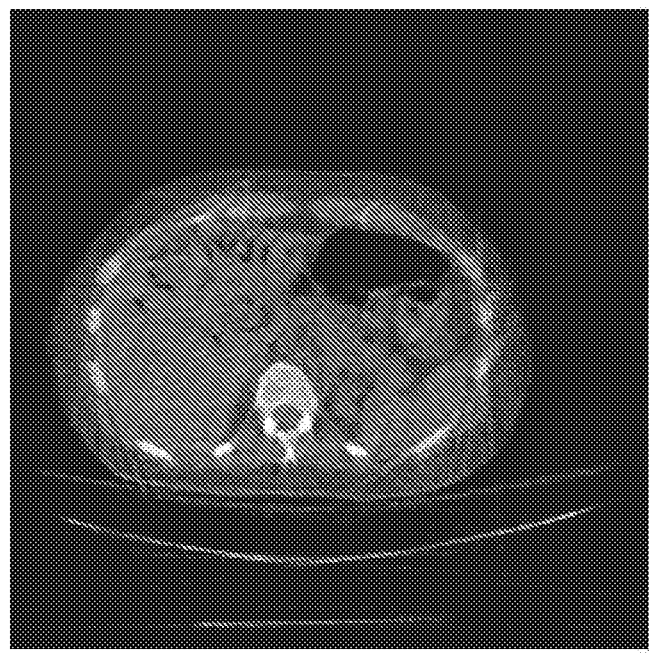
FIG. 23B shows a reconstructed image of the object depicted in FIG. 23A after one iteration of a calibration according to an embodiment of the subject invention.
Figure 23C:
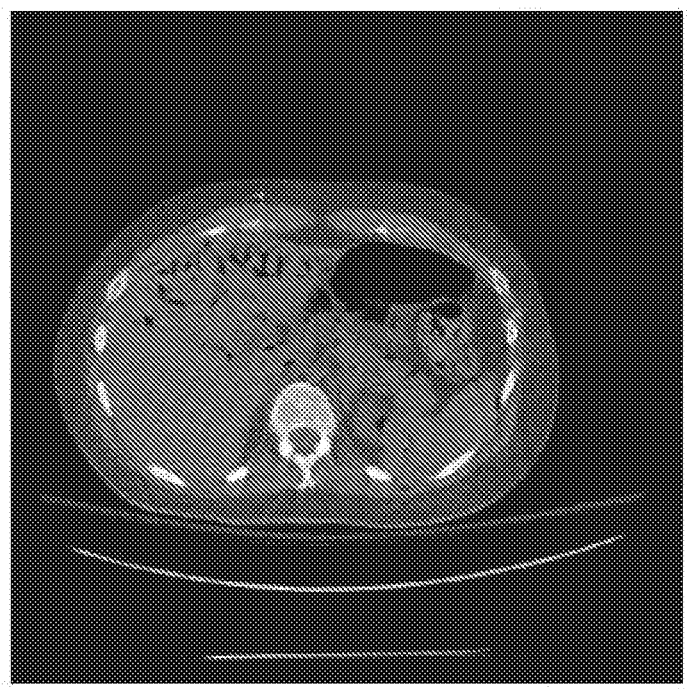
FIG. 23C shows a reconstructed image of the object depicted in FIG. 23A after ten iterations of a calibration according to an embodiment of the subject invention.
Figure 23D:
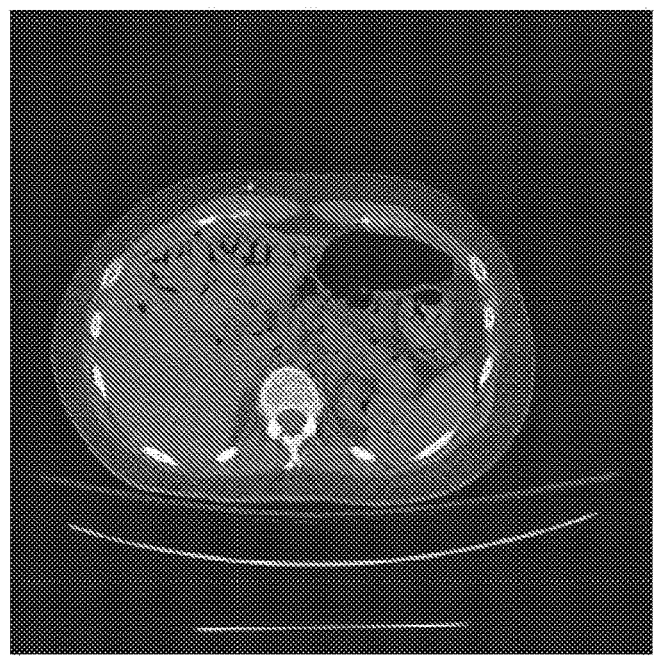
FIG. 23D shows a reconstructed image of the object depicted in FIG. 23A after 20 iterations of a calibration according to an embodiment of the subject invention.
Figure 24A:
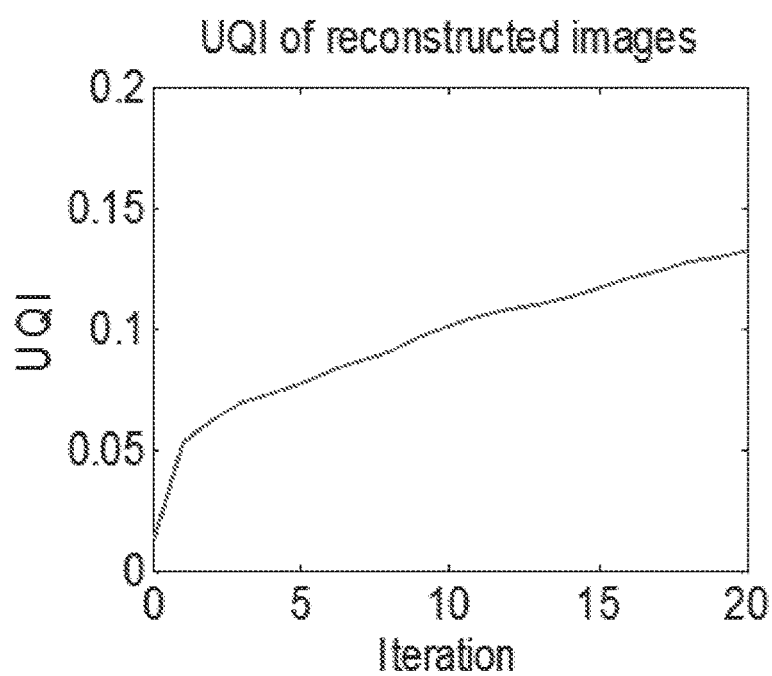
FIG. 24A shows a plot of UQI versus iterations of a calibration according to an embodiment of the subject invention.
Figure 24B:
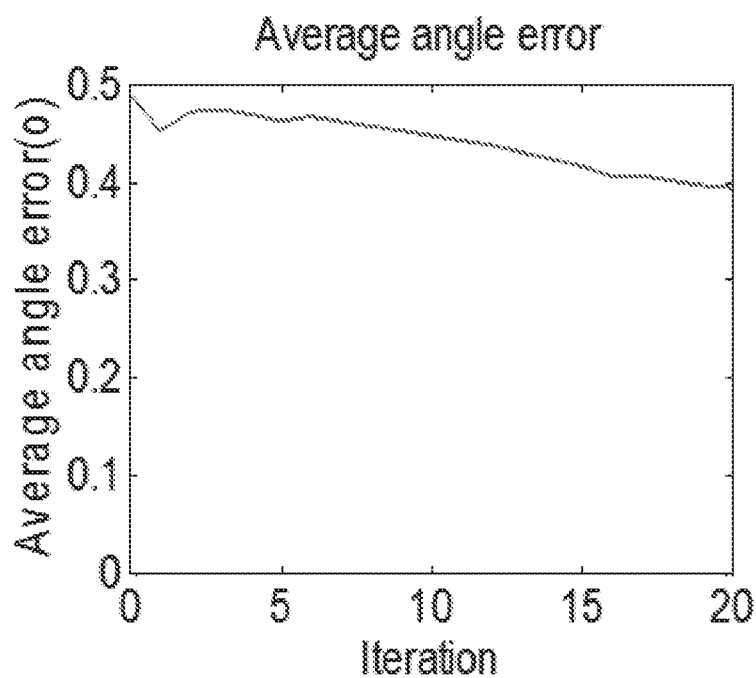
FIG. 24B shows a plot of average angle error (in degrees) versus iterations of a calibration according to an embodiment of the subject invention.
Figure 24C:
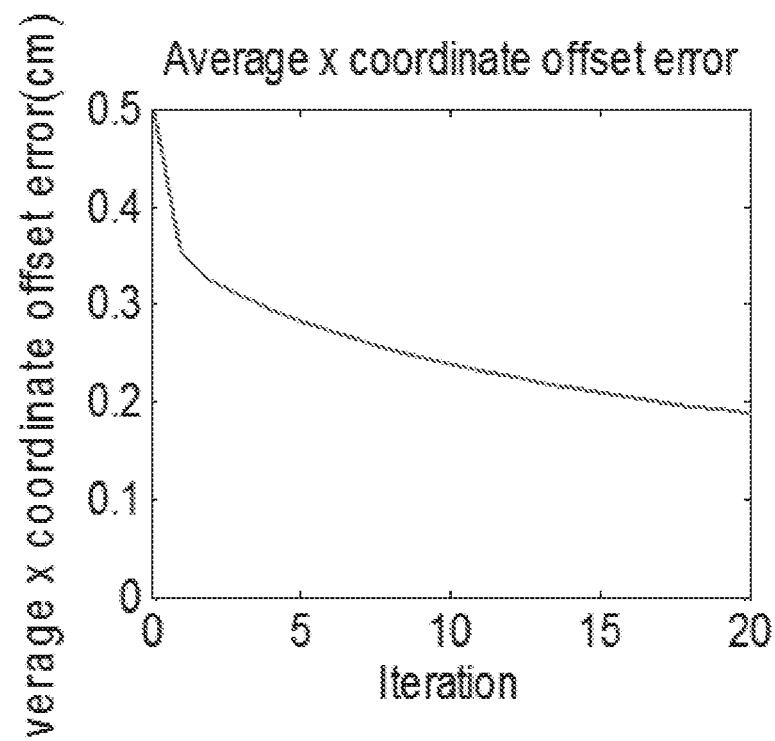
FIG. 24C shows a plot of average x-coordinate offset error (in cm) versus iterations of a calibration according to an embodiment of the subject invention.
Figure 24D:
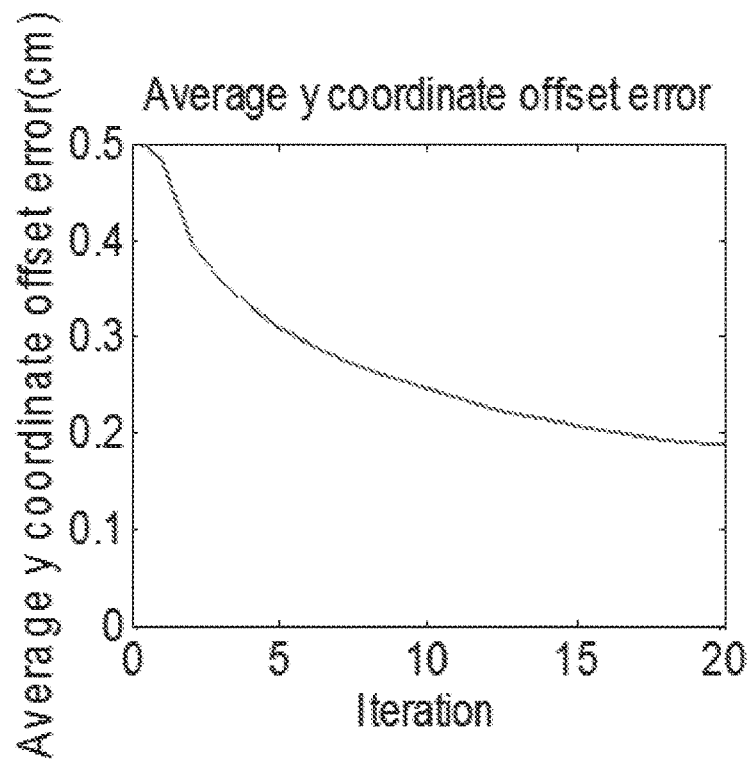
FIG. 24D shows a plot of average y-coordinate offset error (in cm) versus iterations of a calibration according to an embodiment of the subject invention.
Figure 24E:
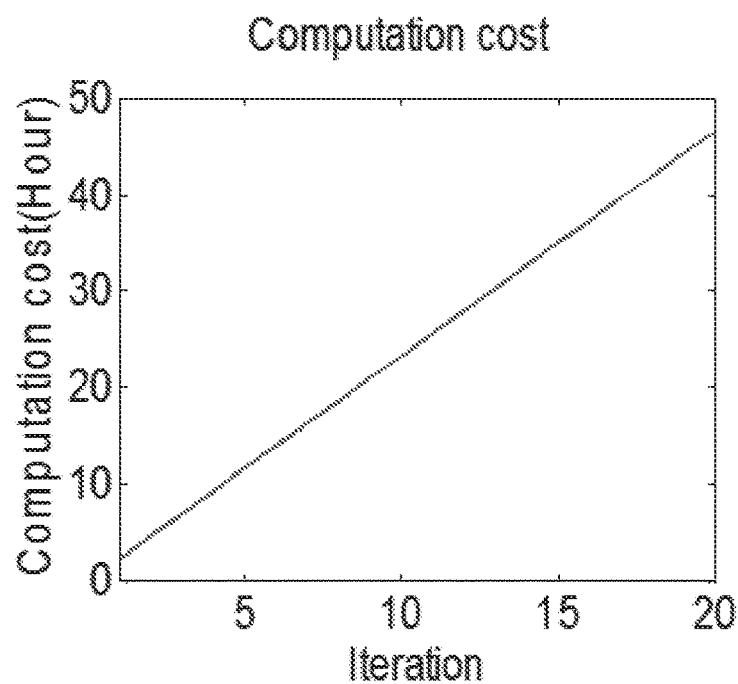
FIG. 24E shows a plot of computation cost (in hours) of reconstructed images versus iteration of a calibration according to an embodiment of the subject invention.
Figure 24F:
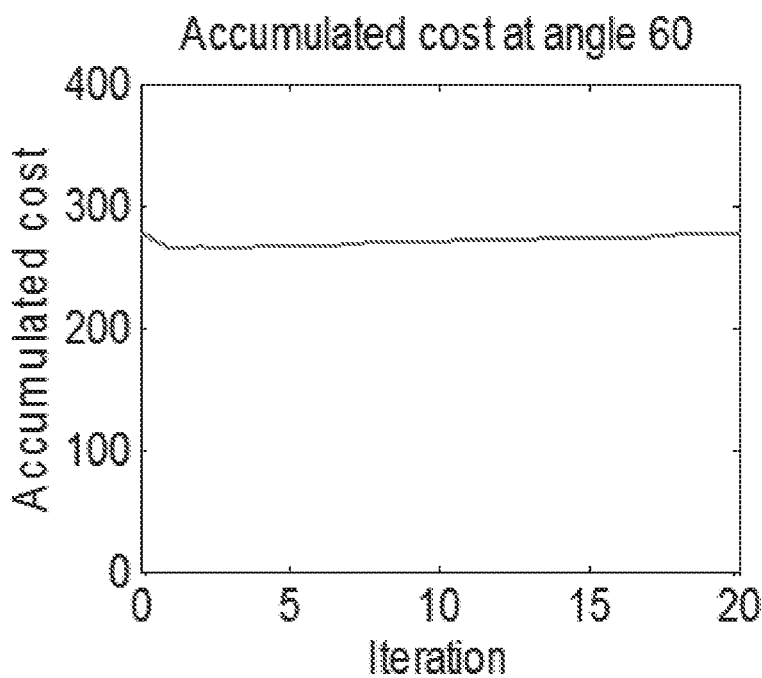
FIG. 24F shows a plot of accumulated cost at angle 60 of reconstructed images versus iteration of a calibration according to an embodiment of the subject invention.

FIG. 23A shows the reconstructed image before any compensation. FIG. 23B shows the reconstructed image of FIG. 23A after one iteration of the calibration; FIG. 23C shows the reconstructed image after ten iterations; and FIG. 23D shows the reconstructed image after 20 iterations. FIG. 24A shows a plot of UQI versus iteration of the calibration according to an embodiment of the subject invention; FIG. 24B shows a plot of average angle error (in degrees) versus iteration of the calibration; FIG. 24C shows a plot of average x-coordinate offset error (in cm) versus iteration of the calibration; FIG. 24D shows a plot of average y-coordinate offset error (in cm) versus iteration of the calibration; FIG. 24E shows a plot of computation cost (in hours) of reconstructed images versus iteration of the calibration; and FIG. 24F shows a plot of accumulated cost at angle 60° of reconstructed images versus iteration of the calibration.

Figure 25A:
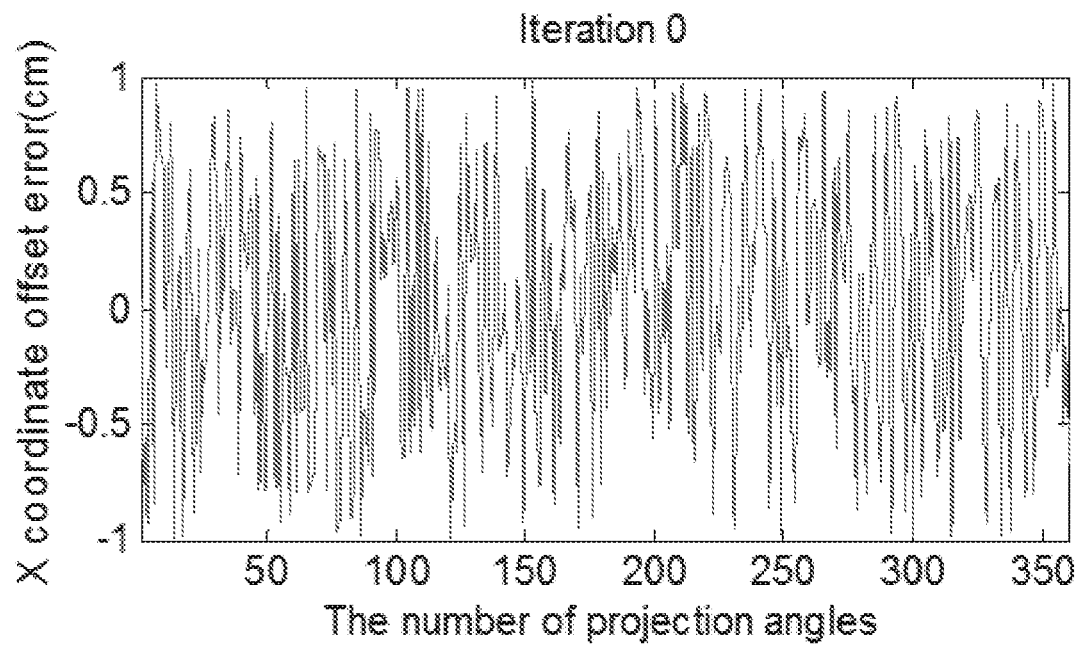
FIG. 25A shows a plot of x-coordinate offset error (in cm) versus the number of projection angles before any calibration (iteration 0).
Figure 25B:
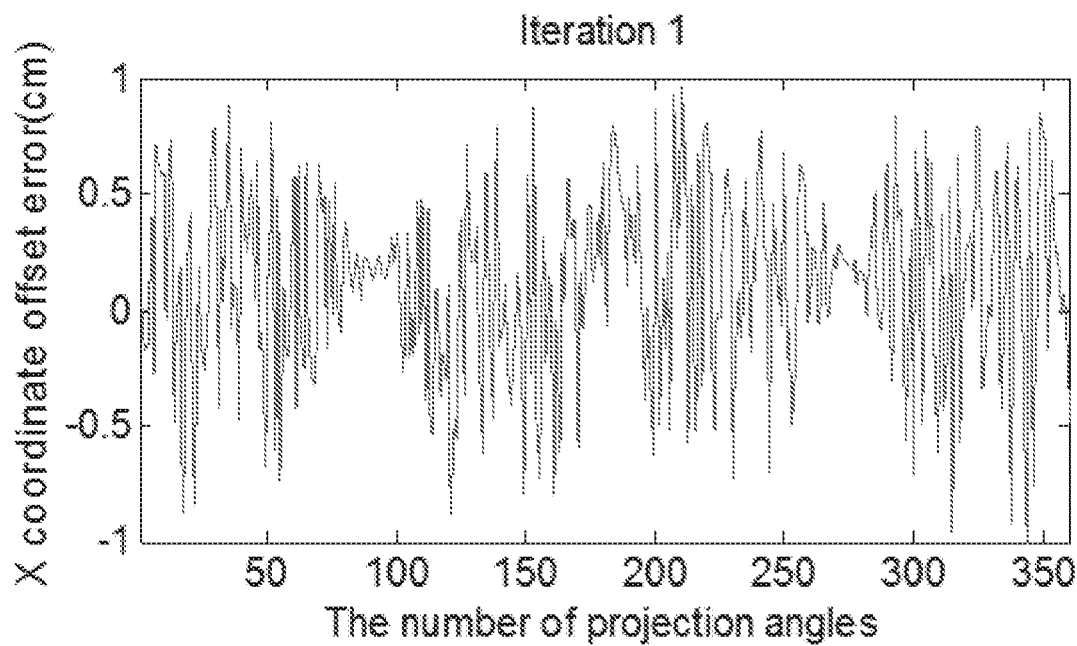
FIG. 25B shows a plot of x-coordinate offset error (in cm) versus the number of projection angles after one iteration of calibration according to an embodiment of the subject invention.
Figure 25C:
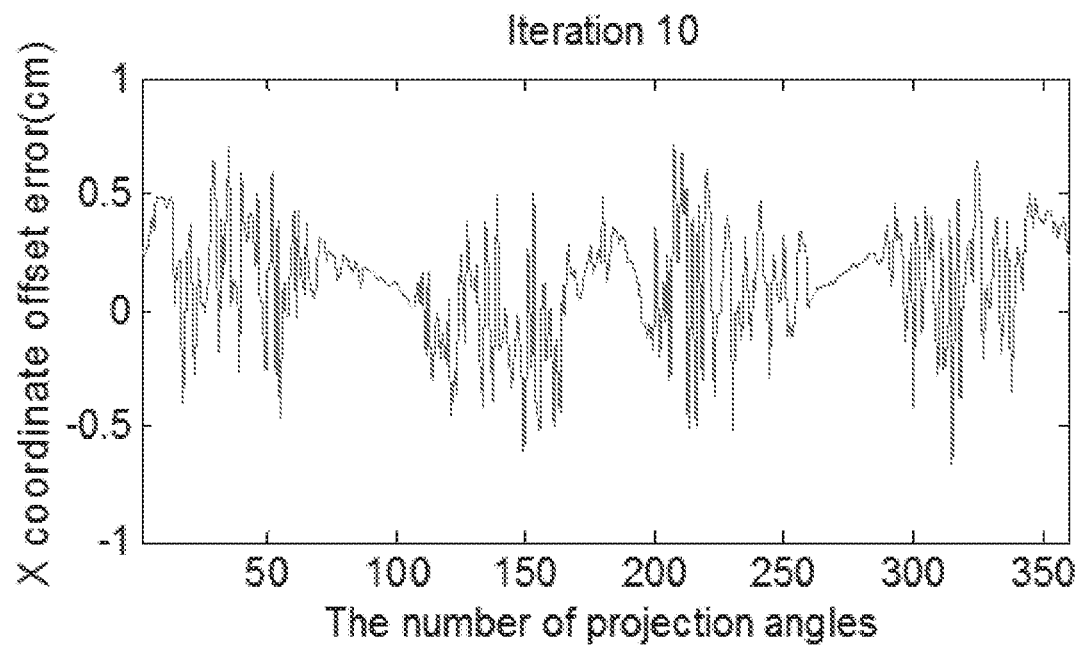
FIG. 25C shows a plot of x-coordinate offset error (in cm) versus the number of projection angles after ten iterations of calibration according to an embodiment of the subject invention.
Figure 25D:
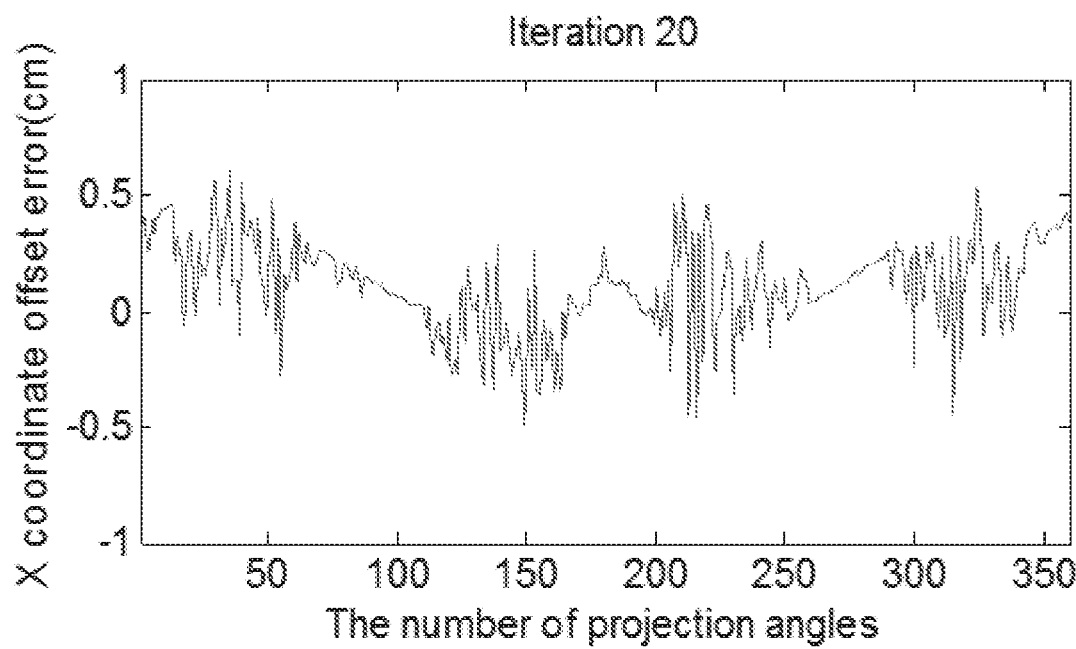
FIG. 25D shows a plot of x-coordinate offset error (in cm) versus the number of projection angles after 20 iterations of calibration according to an embodiment of the subject invention.
Figure 26A:
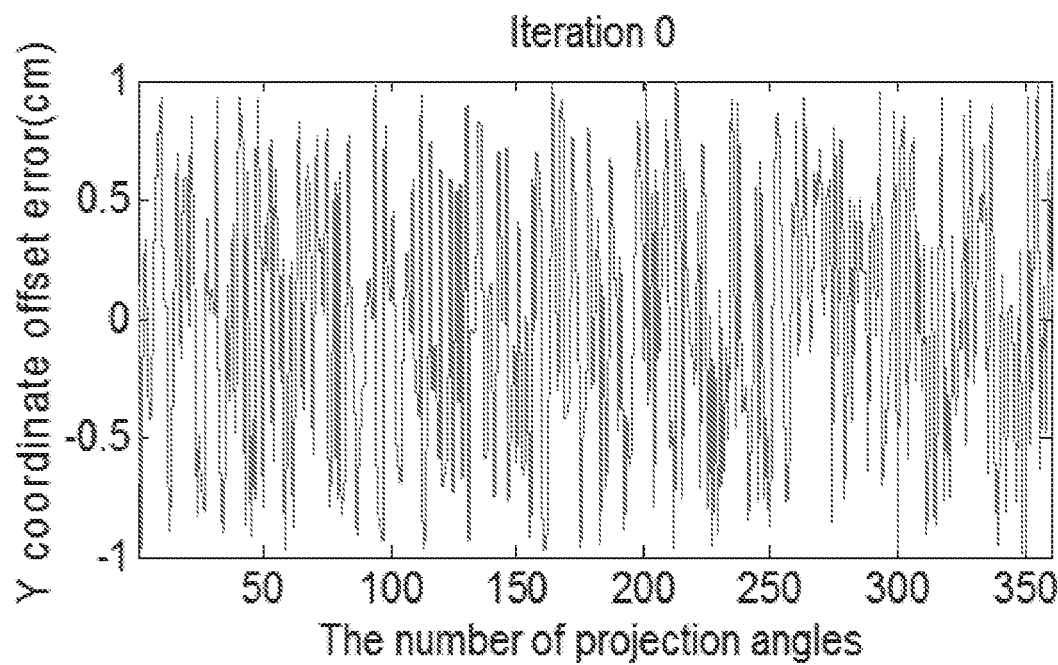
FIG. 26A shows a plot of y-coordinate offset error (in cm) versus the number of projection angles before any calibration (iteration 0).
Figure 26B:
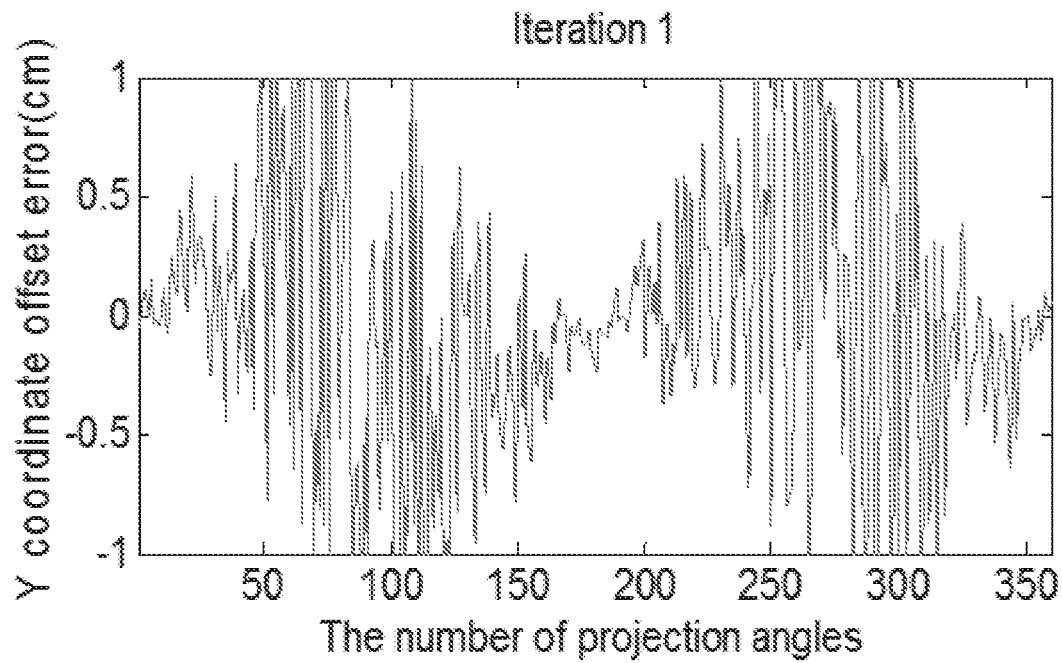
FIG. 26B shows a plot of y-coordinate offset error (in cm) versus the number of projection angles after one iteration of calibration according to an embodiment of the subject invention.
Figure 26C:
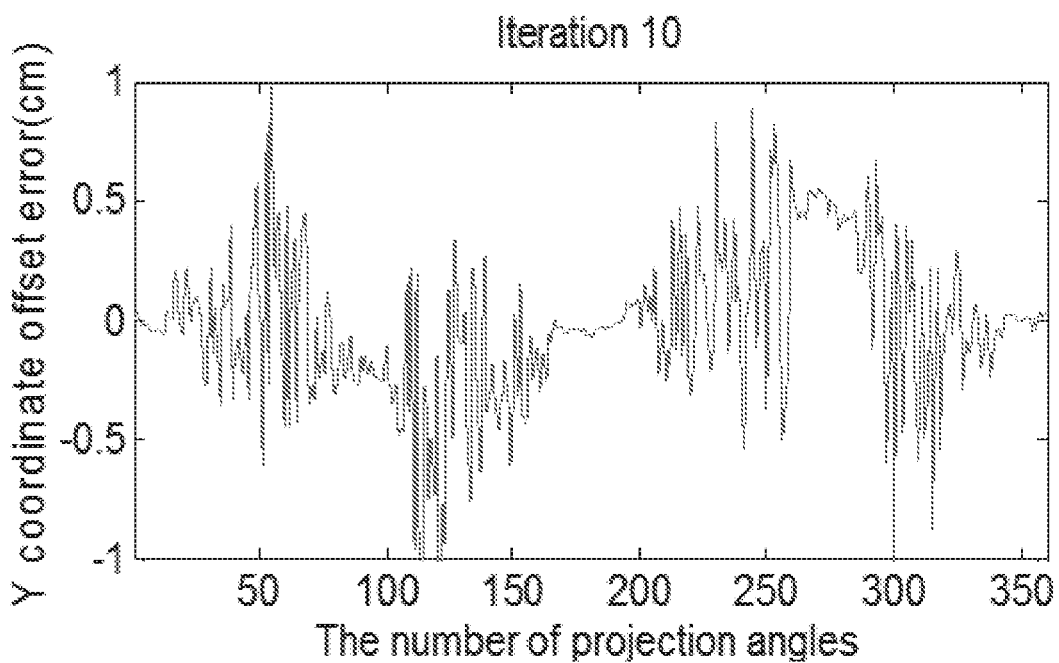
FIG. 26C shows a plot of y-coordinate offset error (in cm) versus the number of projection angles after ten iterations of calibration according to an embodiment of the subject invention.
Figure 26D:
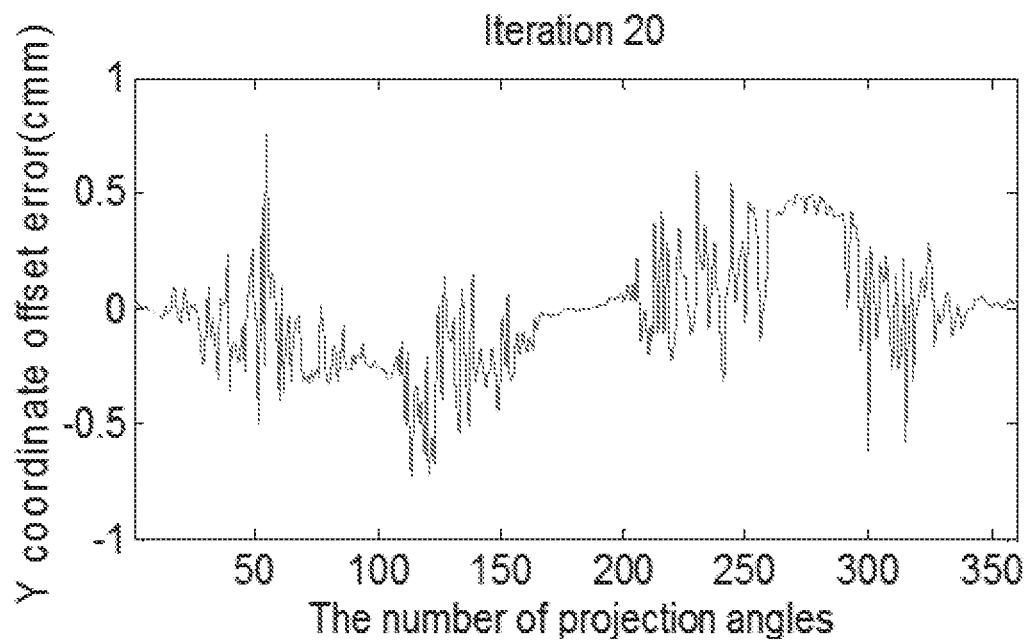
FIG. 26D shows a plot of y-coordinate offset error (in cm) versus the number of projection angles after 20 iterations of calibration according to an embodiment of the subject invention.
Figure 27A:
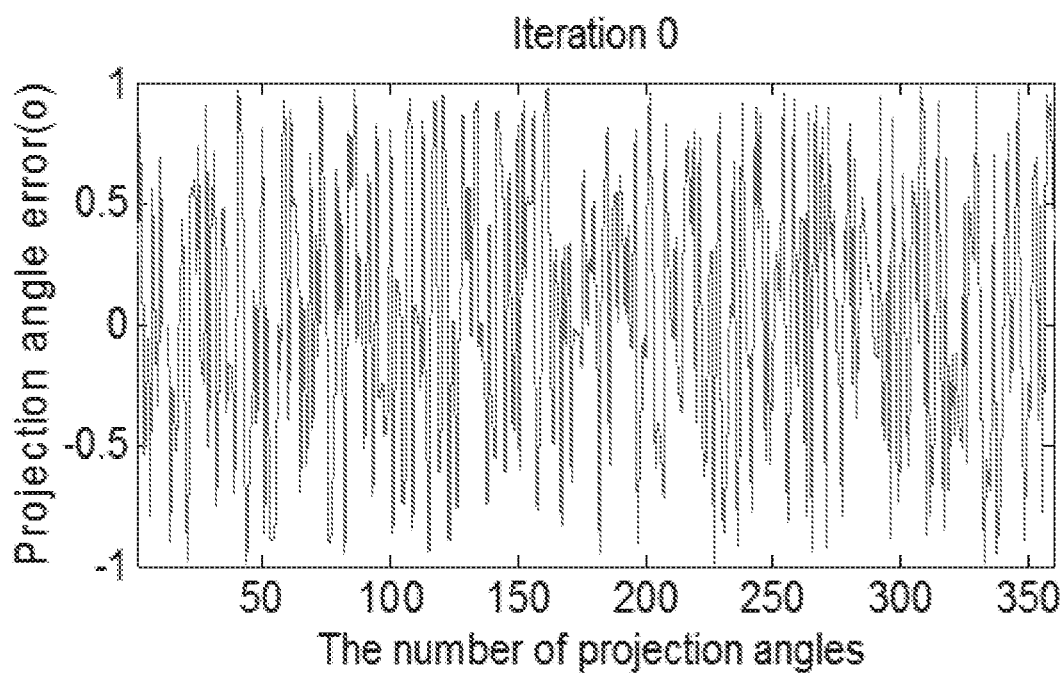
FIG. 27A shows a plot of projection angle error (in degrees) versus the number of projection angles before any calibration (iteration 0).
Figure 27B:
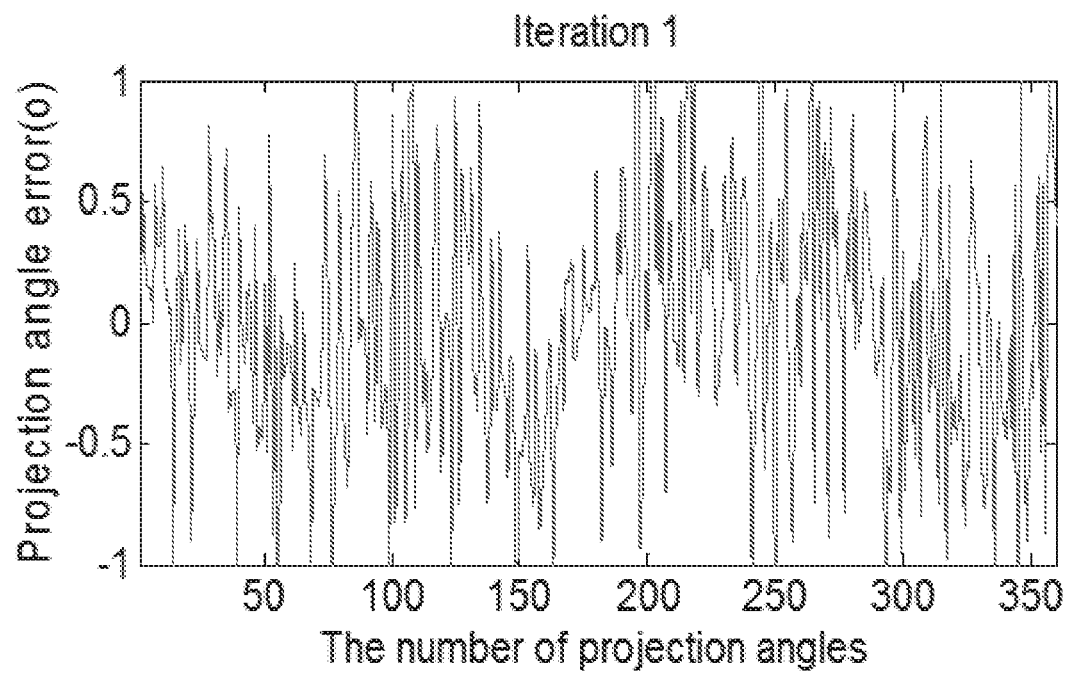
FIG. 27B shows a plot of projection angle error (in degrees) versus the number of projection angles after one iteration of calibration according to an embodiment of the subject invention.
Figure 27C:
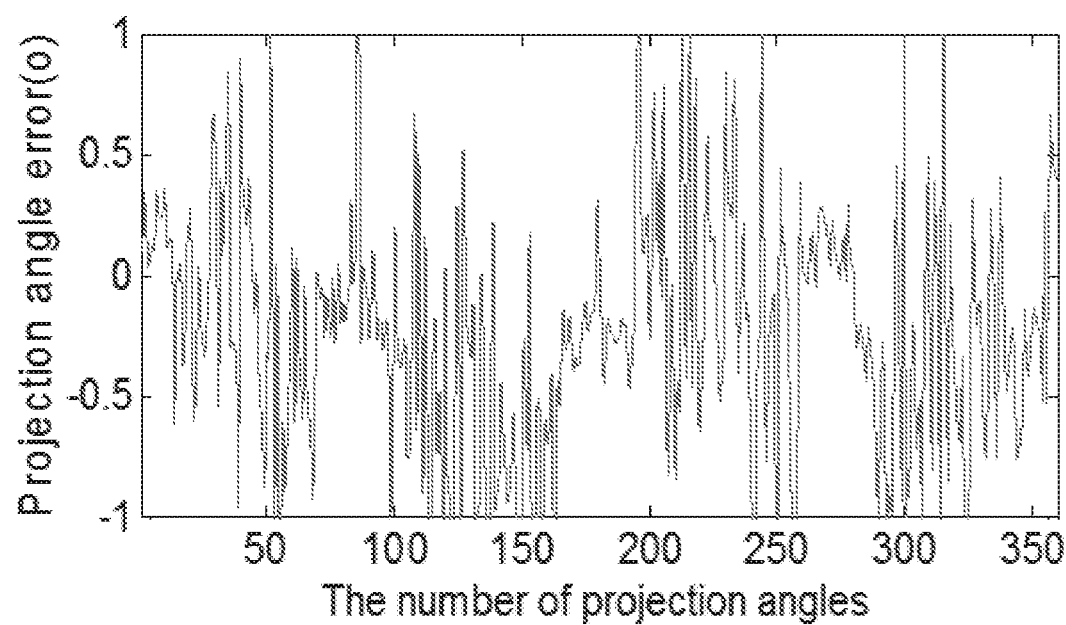
FIG. 27C shows a plot of projection angle error (in degrees) versus the number of projection angles after ten iterations of calibration according to an embodiment of the subject invention.
Figure 27D:
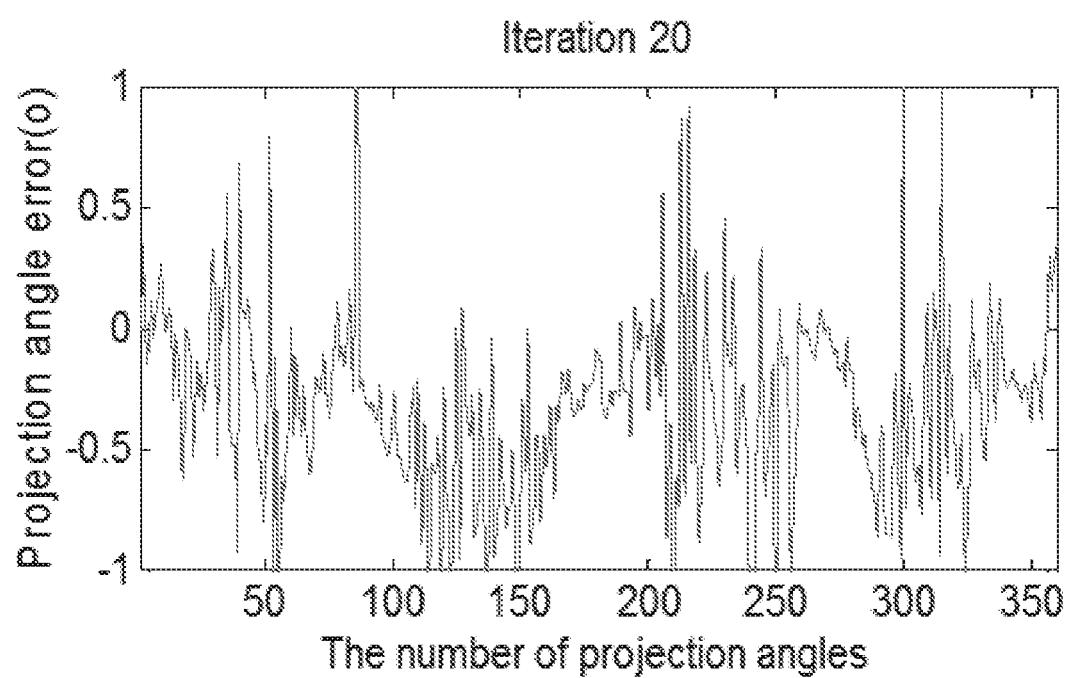
FIG. 27D shows a plot of projection angle error (in degrees) versus the number of projection angles after 20 iterations of calibration according to an embodiment of the subject invention.

FIG. 25A shows a plot of x-coordinate offset error (in cm) versus the number of projection angles before any calibration (iteration 0); FIG. 25B shows a plot of x-coordinate offset error (in cm) versus the number of projection angles after one iteration of the calibration; FIG. 25C shows a plot of x-coordinate offset error (in cm) versus the number of projection angles after ten iterations; and FIG. 25D shows a plot of x-coordinate offset error (in cm) versus the number of projection angles after 20 iterations. FIG. 26A shows a plot of y-coordinate offset error (in cm) versus the number of projection angles before any calibration (iteration 0); FIG. 26B shows a plot of y-coordinate offset error (in cm) versus the number of projection angles after one iteration of the calibration; FIG. 26C shows a plot of y-coordinate offset error (in cm) versus the number of projection angles after ten iterations; and FIG. 26D shows a plot of y-coordinate offset error (in cm) versus the number of projection angles after 20 iterations. FIG. 27A shows a plot of projection angle error (in degrees) versus the number of projection angles before any calibration (iteration 0); FIG. 27B shows a plot of projection angle error (in degrees) versus the number of projection angles after one iteration of the calibration; FIG. 27C shows a plot of projection angle error (in degrees) versus the number of projection angles after ten iterations; and FIG. 27D shows a plot of projection angle error (in degrees) versus the number of projection angles after 20 iterations.

Referring to FIGS. 23A-23D, 24A-24F, 25A-25D, 26A-26D, and 27A-27D, it can be seen that all parameters and characteristics of the reconstructed image improved significantly with the calibration process. For many parameters, only a small number of iterations was needed to see drastic improvement.

Geometric parameters have different sensitivities on reconstruction quality. In a geometric calibration, detector offset significantly affects reconstruction. Detector tilt and projection angular error have stronger effects than the SOD error and the ODD errors on reconstruction quality. This can help explain the calibration results for detector offset, detector tilt, and projection angle being better than those for SOD and ODD. In patient motion calibration, object x- and y-coordinate offsets were more effective on the quality of a reconstructed image than the projection angular error was.

A closely-related issue is the parametric sampling rate for re-projection. The greater the sampling rate, the more accurate the calibration results will be, but the higher computational cost will be involved. Sampling rate can be chosen with balance between calibration results and computational overhead in mind.

An important issue in using TV is its weight. If it is too small, TV will not be able to reduce artifacts and noise. If it is too large, TV will over-smoothen CT images. The TV parameter depends on levels of artifacts and noise. In Examples 1-3, the TV parameter was empirically set to 0.1 after geometric calibration. A smaller TV parameter could be used in a case of weaker noise.

Example 4

Figure 2A:
FIG. 2A shows an image of a Shepp-Logan phantom before any compensation.
Figure 2B:
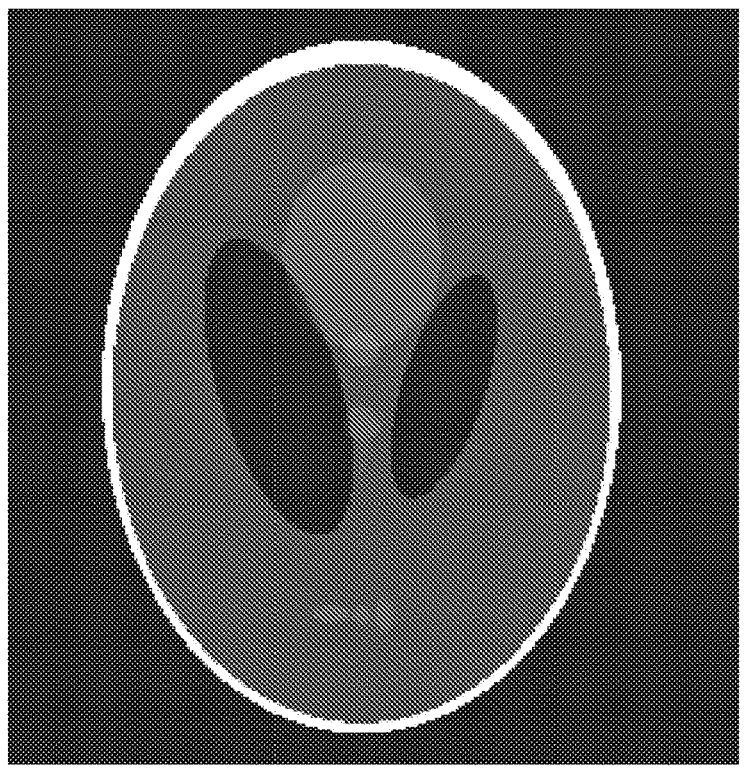
FIG. 2B shows an image of the phantom of FIG. 2A after 25 iterations of a calibration according to an embodiment of the subject invention.
Figure 3:
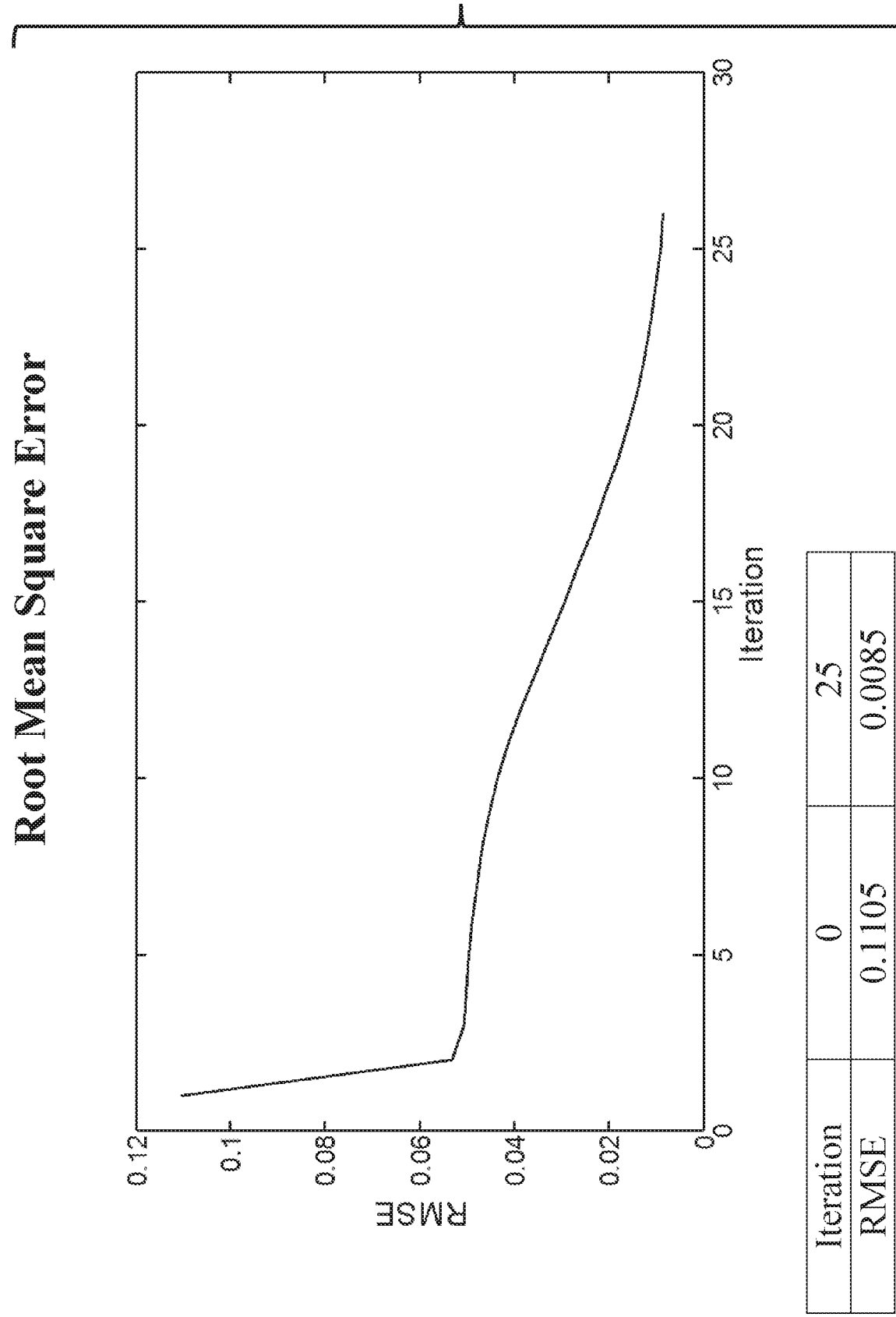
FIG. 3 shows a plot of root mean square error (RMSE) versus iteration of a calibration according to an embodiment of the subject invention.
Figure 4:
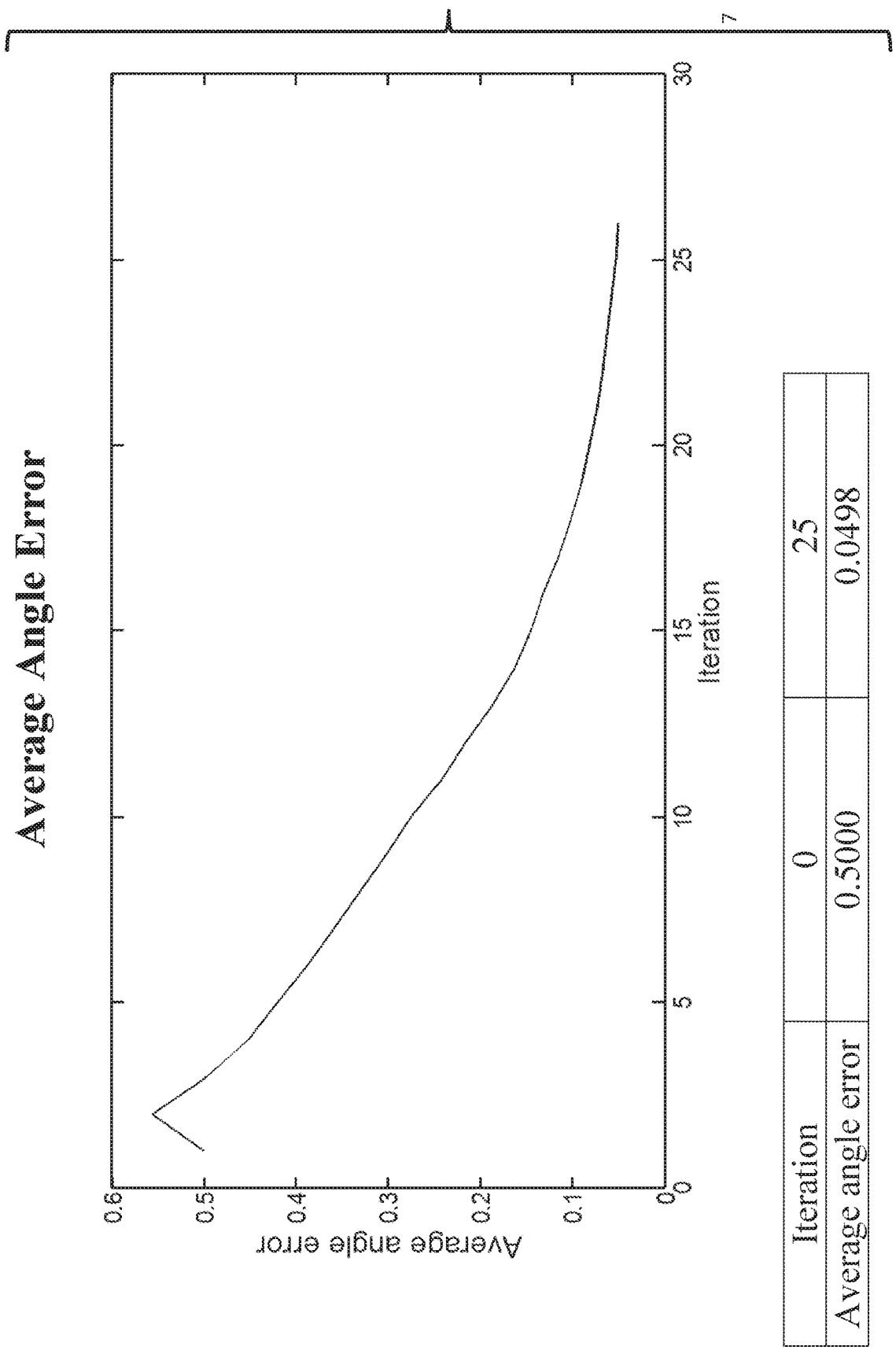
FIG. 4 shows a plot of average angle error versus iteration of a calibration according to an embodiment of the subject invention.
Figure 5A:
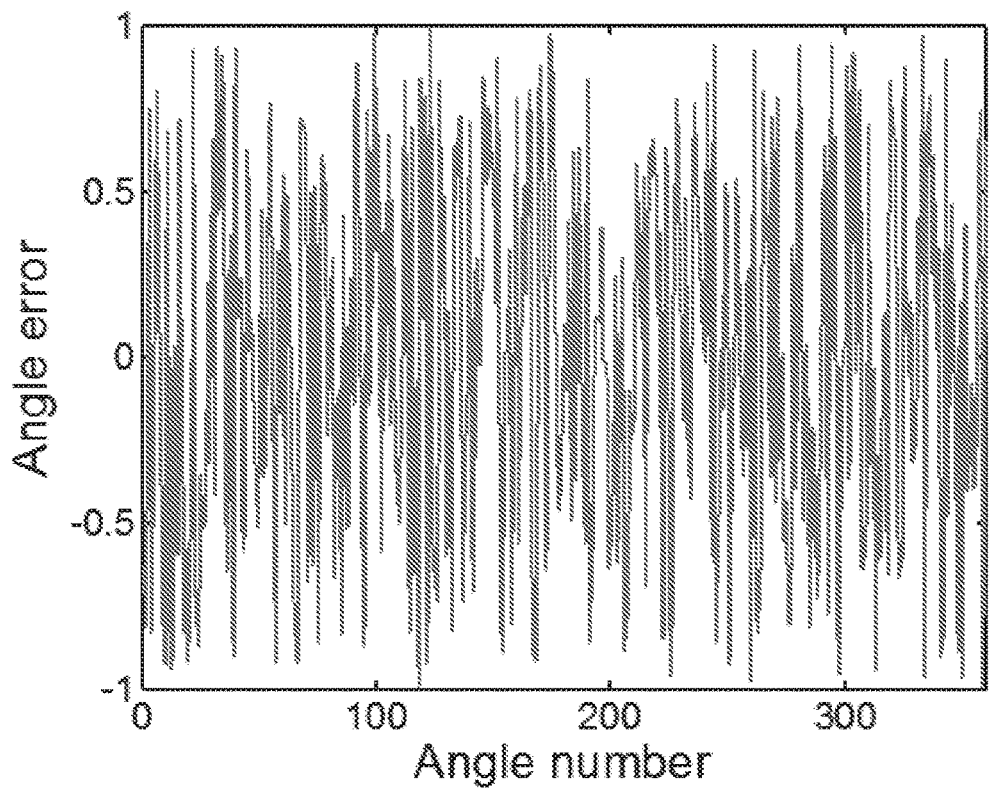
FIG. 5A shows a plot of angle error versus angle number.
Figure 5B:
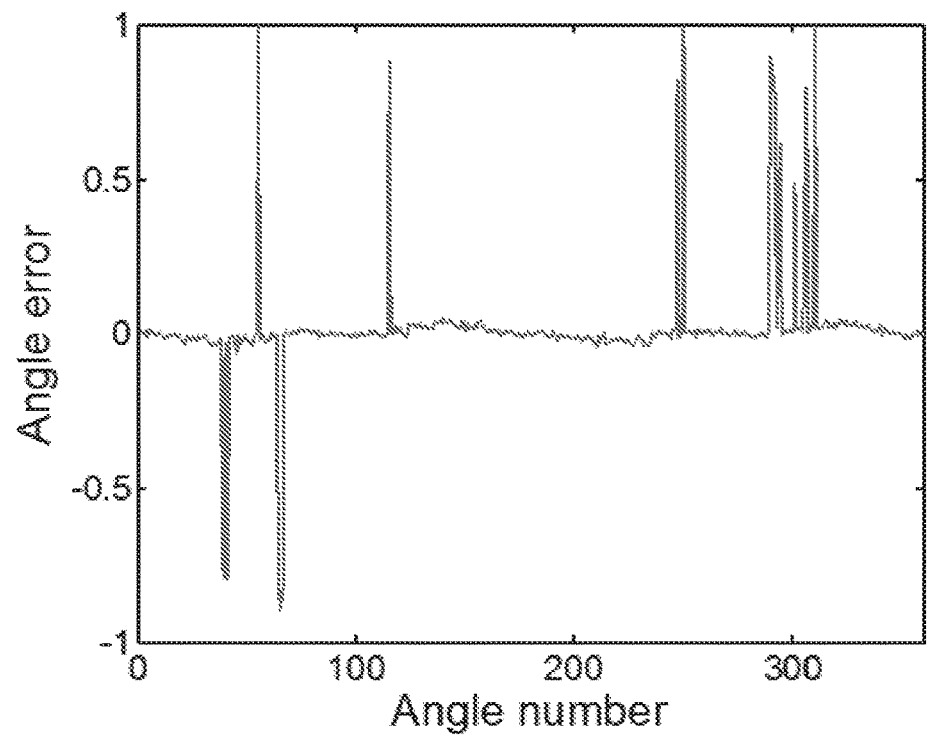
FIG. 5B shows a plot of angle error versus angle number of a calibration according to an embodiment of the subject invention.
Figure 6:
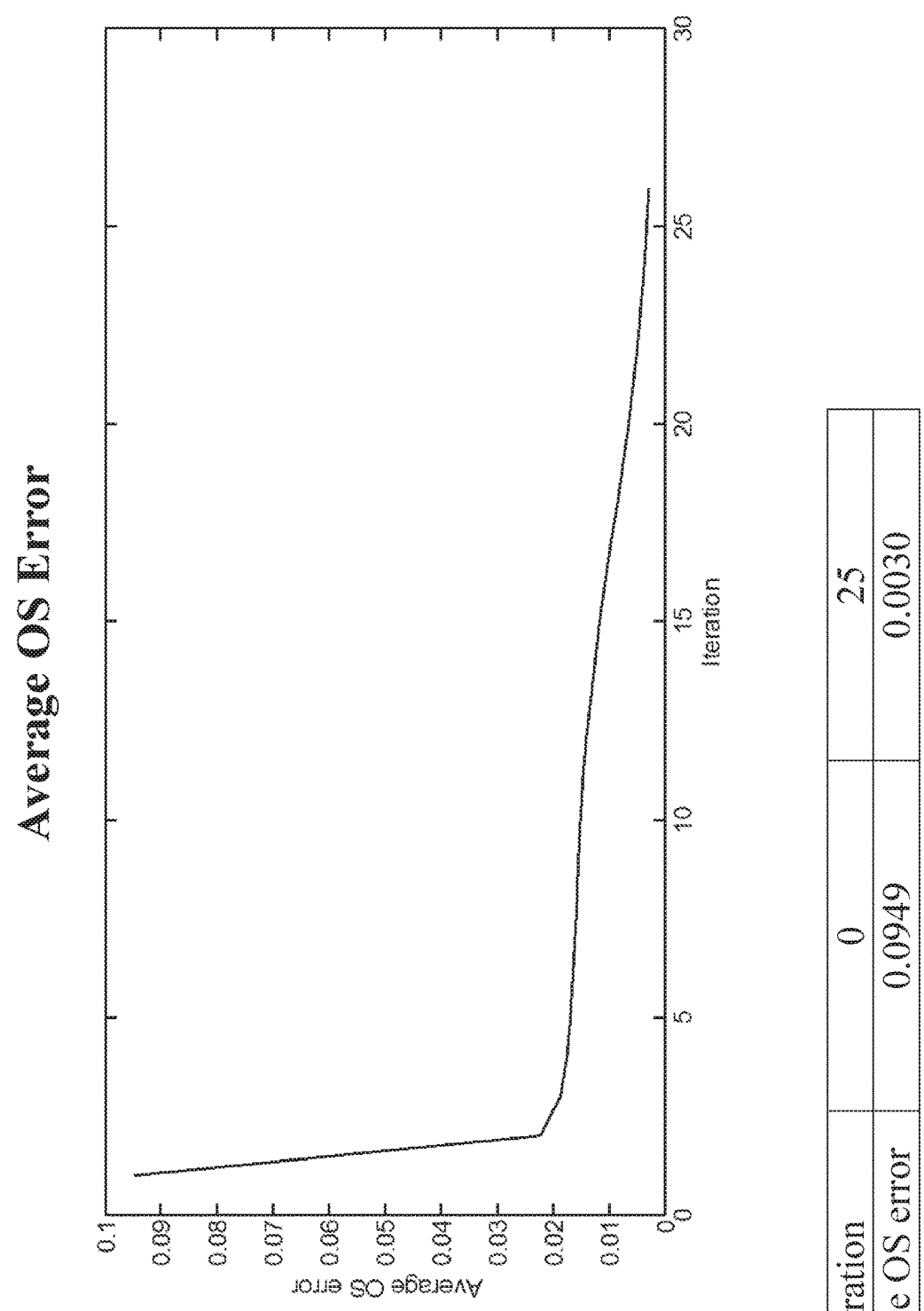
FIG. 6 shows a plot of average original source-object distance (OS) error versus iteration of a calibration according to an embodiment of the subject invention.
Figure 7A:
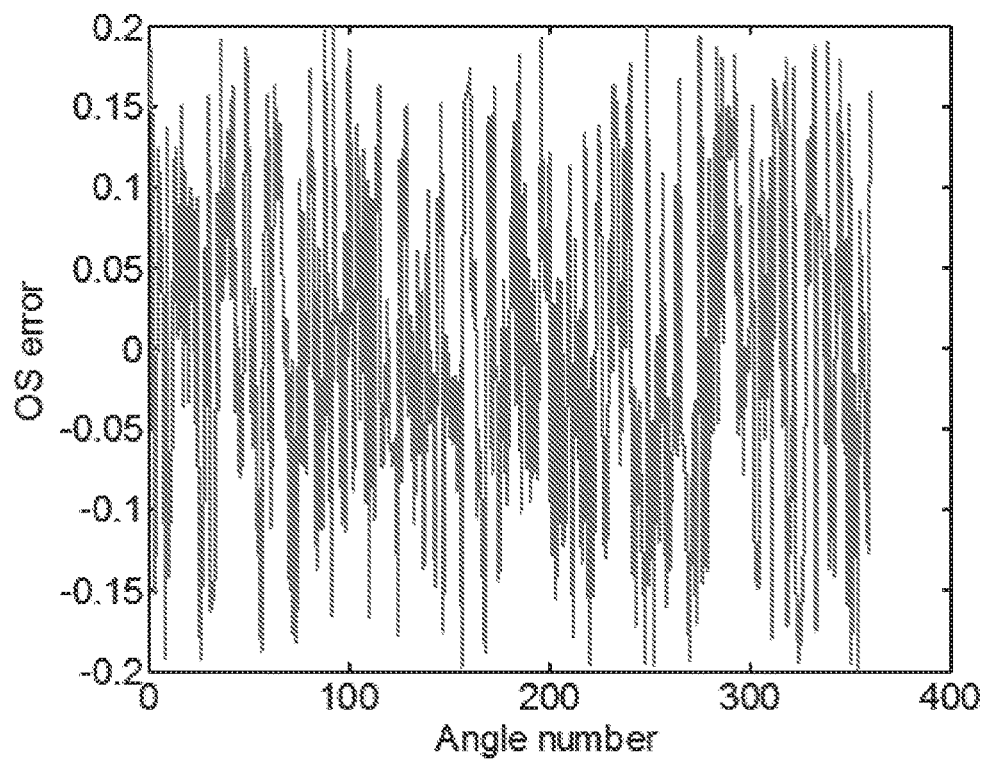
FIG. 7A shows a plot of OS error versus angle number.
Figure 7B:
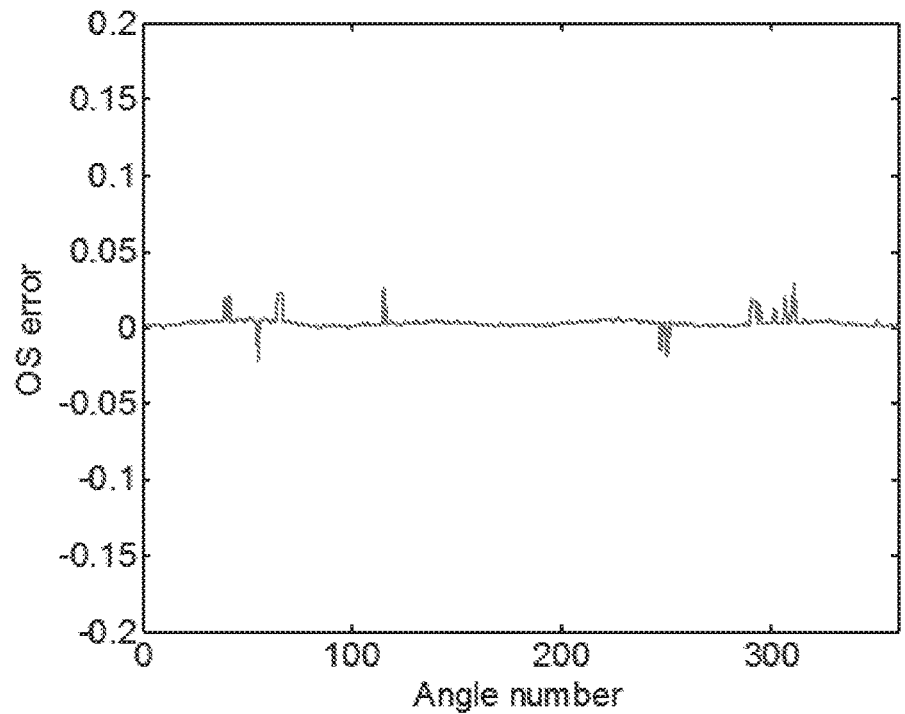
FIG. 7B shows a plot of OS error versus angle number of a calibration according to an embodiment of the subject invention.
Figure 8:
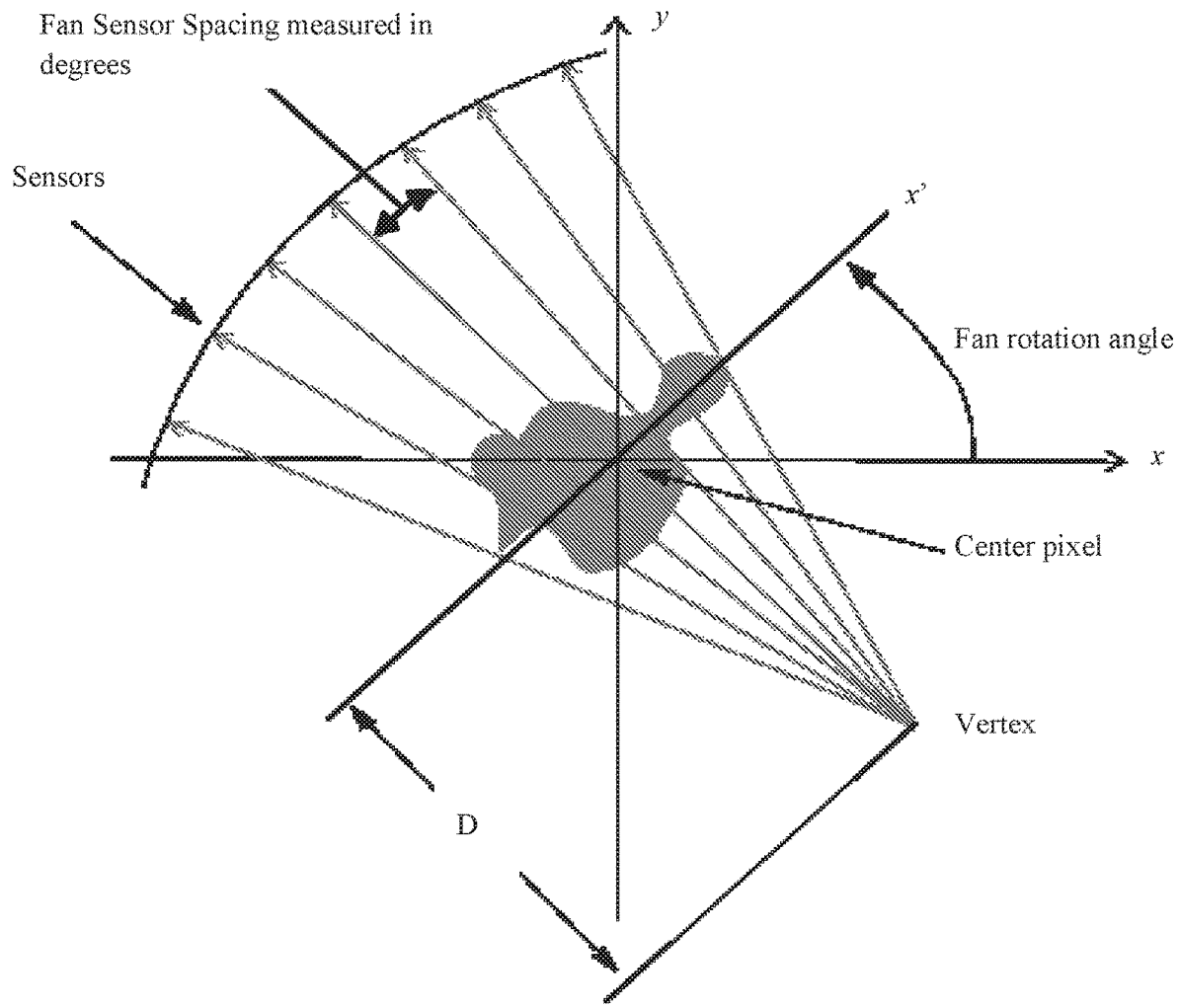
FIG. 8 shows a schematic view illustrating spectral computed tomography (CT).

The LLE-based calibration approach was evaluated using a Shepp-Logan phantom. FIG. 2A shows the phantom before any calibration, and FIG. 2B shows the reconstructed image after 25 iterations of the calibration. FIG. 3 shows a plot of root mean square error (RMSE) versus iteration of the calibration, and FIG. 4 shows a plot of average angle error versus iteration of the calibration. FIG. 5A shows a plot of angle error versus angle number for this calibration, and FIG. 5B shows a plot of angle error versus angle number of the calibration. FIG. 6 shows a plot of average original SOD (OS) error versus iteration of the calibration; FIG. 7A shows a plot of OS error versus angle number; and FIG. 7B shows a plot of OS error versus angle number of the calibration.

Referring to FIGS. 2A-2B, 3, 4, 5A-5B, 6, and 7A-7B, it can be seen that all parameters and characteristics of the reconstructed image improved significantly with the calibration process. For many parameters, only a small number of iterations was needed to see drastic improvement.

Example 5

Figure 9:
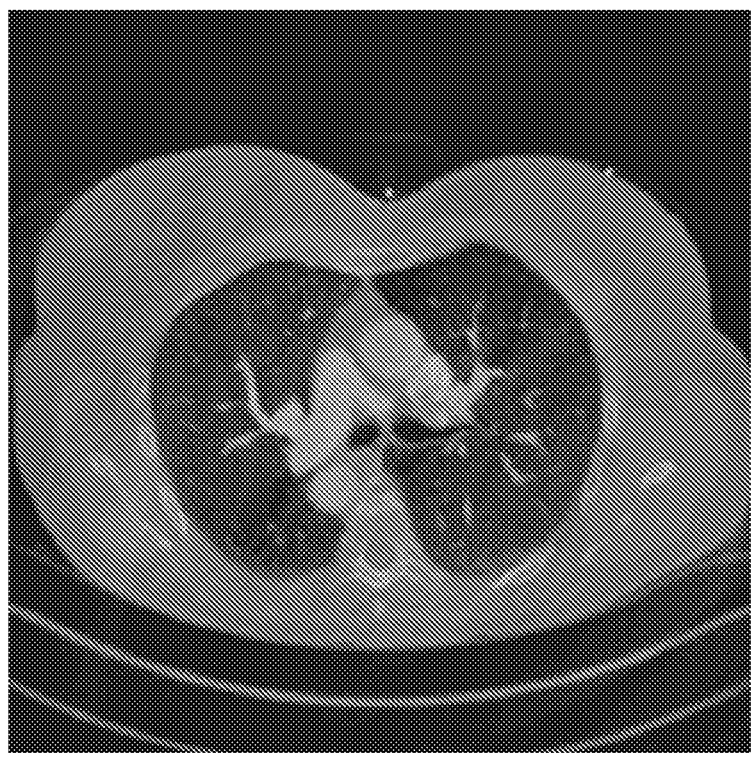
FIG. 9 shows an original image of a chest phantom before any compensation.
Figure 10A:
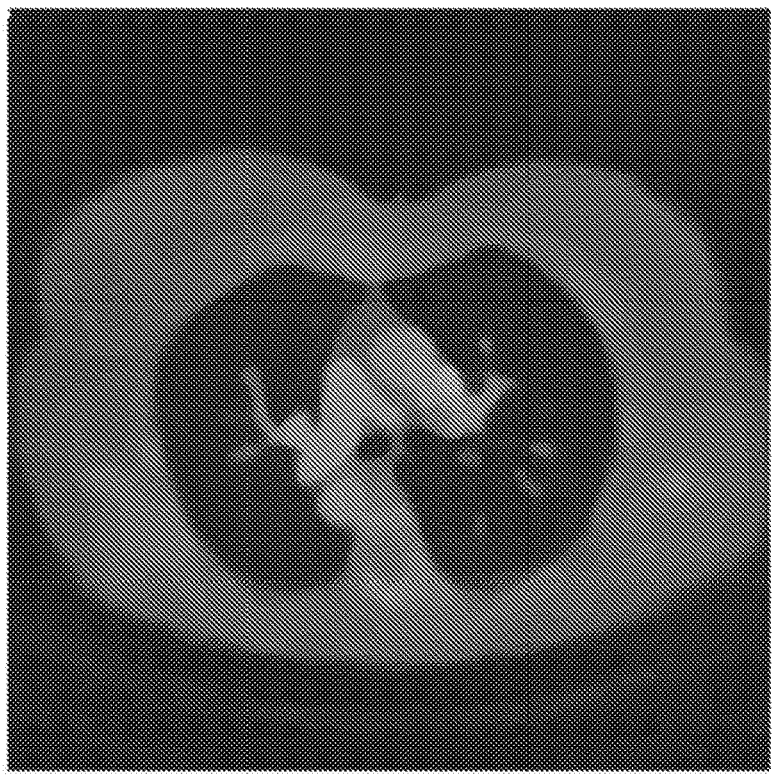
FIG. 10A shows an image of a chest phantom before any compensation.
Figure 10B:
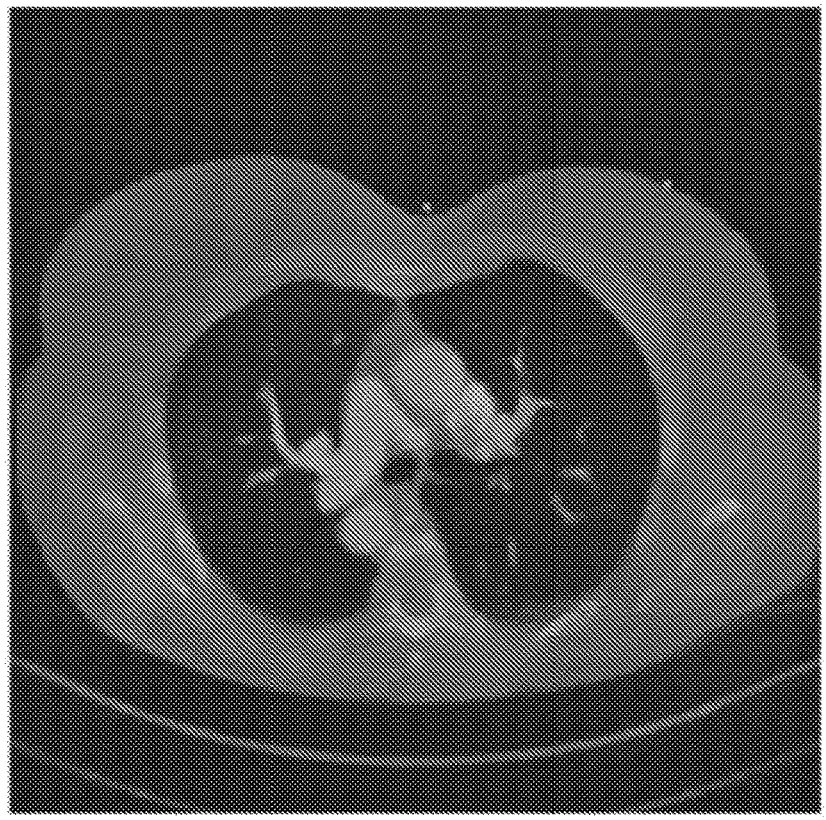
FIG. 10B shows an image of the phantom of FIG. 10A after 6 iterations of a calibration according to an embodiment of the subject invention.
Figure 11:
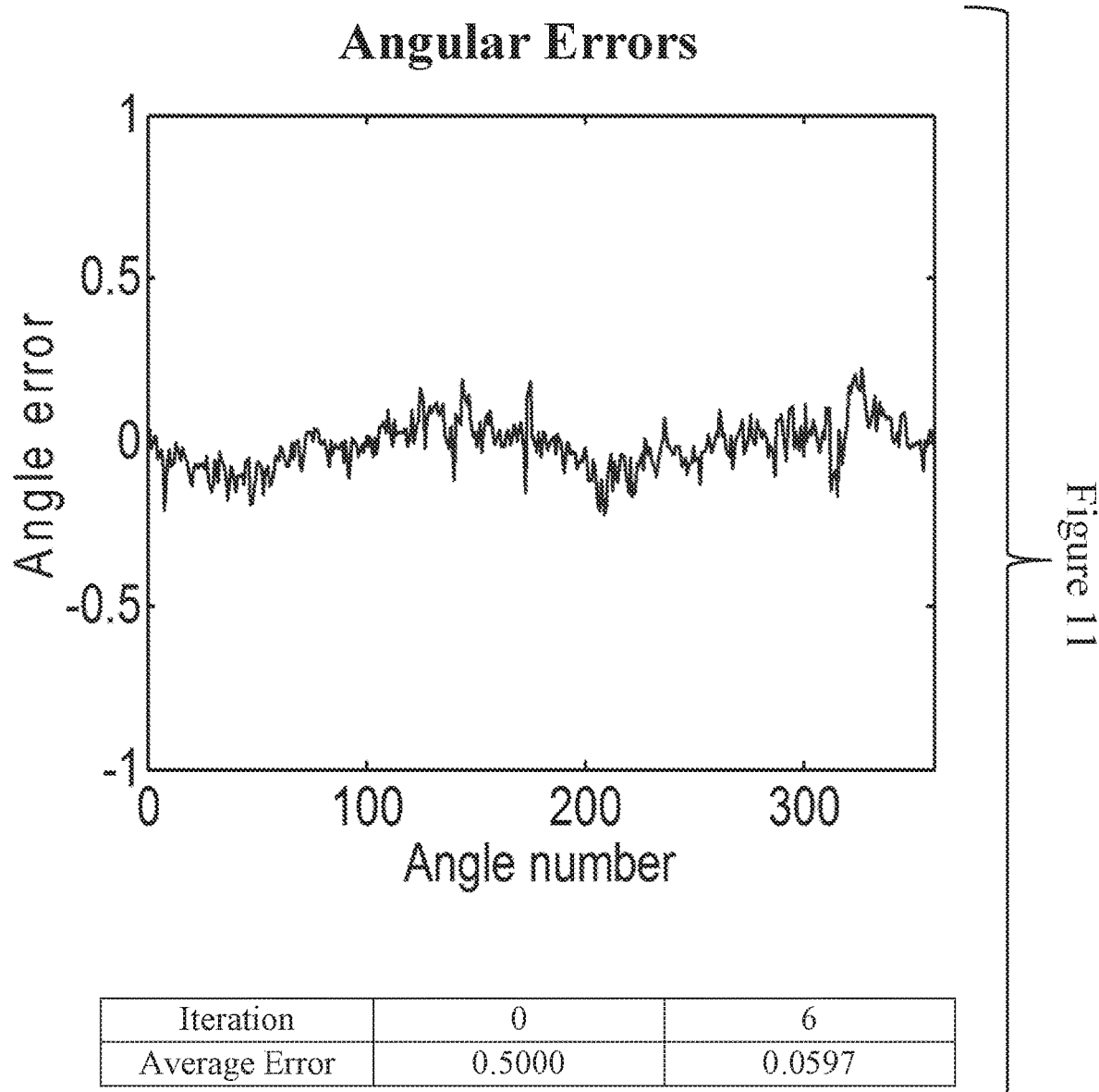
FIG. 11 shows a plot of angle error versus angle number of a calibration according to an embodiment of the subject invention.
Figure 12:
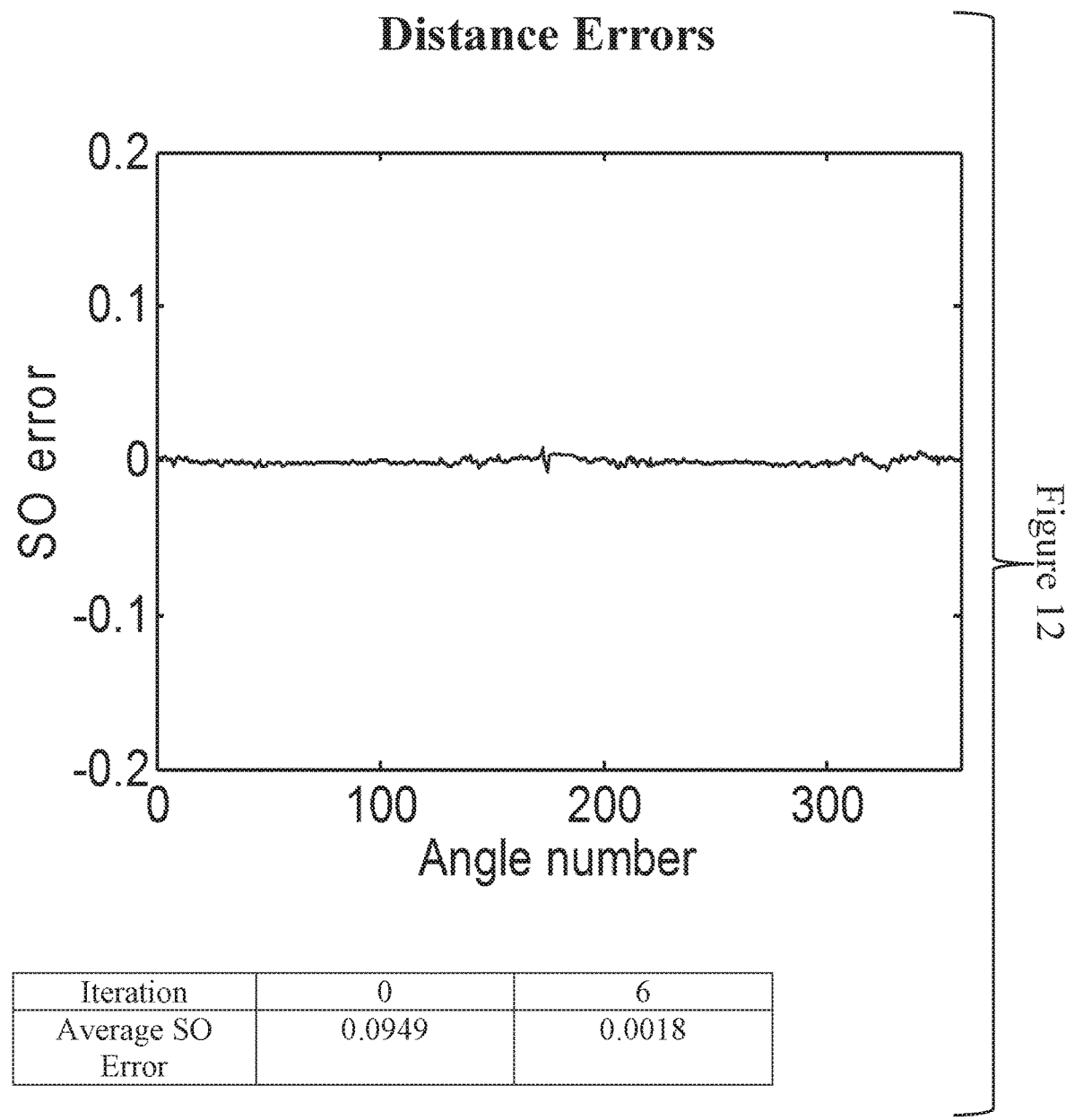
FIG. 12 shows a plot of OS error versus angle number of a calibration according to an embodiment of the subject invention.

The LLE-based calibration approach was evaluated using a chest phantom with Poisson noise of $10^5$ photons. FIG. 9 shows an image of the chest phantom used in this example. FIG. 10A shows an image of the chest phantom before any compensation, and FIG. 10B shows the image of the phantom after 6 iterations of the calibration. FIG. 11 shows a plot of angle error versus angle number of the calibration, and FIG. 12 shows a plot of OS error versus angle number of the calibration.

Referring to FIGS. 10A-10B, 11, and 12, it can be seen that the calibration process improved the reconstructed image.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

G. Wang, H. Yu, and B. D. Man. "An outlook on x-ray CT research and development." Medical physics 35.3 (2008): 1051-1064.

G. Wang, S. Zhao, and H. Yu, et al., "Design, analysis and simulation for development of the first clinical micro-CT scanner." Academic Radiol. 12.4 (2005):511-525.

C. Rock, U. Linsenmaier, R. Brandl, et al. "Introduction of a new mobile C-arm/CT combination equipment (ISO-C-3D). Initial results of 3-D sectional imaging." Der Unfallchirurg 104.9 (2001): 827-833.

G. Rajiv, M. Grasruck, C. Suess, et al. "Ultra-high resolution flat-panel volume CT: fundamental principles, design architecture, and system characterization." European radiology 16.6 (2006): 1191-1205.

F. Noo, R. Clackdoyle, C. Mennessier, et al. "Analytic method based on identification of ellipse parameters for scanner calibration in cone-beam tomography." Phys. Med. Biol. 45 (2000) 3489-3508.

D. Panetta, N. Belcari, A. D. Guerra, et al. "An optimization-based method for geometrical calibration in cone-beam CT without dedicated phantoms." Med. Biol. 53 (2008) 3841-3861.

W. Wein, A. Ladikos, A. Baumgartner. "Self-calibration of geometric and radiometric parameters for cone-beam computed tomography." in: Fully 3D, Potsdam, (2011): 327-330.

V. Patel, R. N. Chityala, K. R. Hoffmann, et al. "Self-calibration of a cone-beam micro-CT system." Med. Phys. 36 (2009) 48-58.

B. D. Man, S. Basu, D. Beque, et al. "Multi-source inverse geometry CT: a new system concept for X-ray computed tomography." Medical Imaging. International Society for Optics and Photonics (2007).

Y. Liu, H. Liu, Y. Wang, et al. "Half-scan cone-beam CT fluoroscopy with multiple sources." Med. Phys. 28.7 (2001):1466-1471.

J. Hsieh. "Computed Tomography, Principles, Design, Artifacts, and Recent Advances. Bellingham." WA: SPIE, 2003.

C. R. Crawford and K. F. King. "Computed-tomography scanning with simultaneous patient translation." Med. Phys. 17.6 (1990): 967-982.

G. Wang and M. W. Vannier. "Preliminary study on helical CT algorithms for patient motion estimation and compensation." IEEE Trans. Med. Imag. 14.2 (1995): 205-211.

W. G. Lu and T. R. Mackie. "Tomographic motion detection and correction directly in sinogram space." Phys., Med., Biol. 47.8 (2002): 1267-1284.

H. Yu, and G. Wang. "Data consistency based rigid motion artifact reduction in fan-beam CT." Medical Imaging, IEEE Transactions on 26.2 (2007): 249-260.

H. Yu, Y. Wei, J. Hsieh, et al. "Data consistency based translational motion artifact reduction in fan-beam CT." Medical Imaging, IEEE Transactions on 25.6 (2006): 792-803.

S. Leng, B. Nett, M. Speidel, et al. "Motion artifact reduction in fan-beam and cone-beam computed tomography via the fan-beam data consistency condition (FDCC)." Medical Imaging. International Society for Optics and Photonics, 2007.

S. T. Roweis, and S. K. Lawrence. "Nonlinear dimensionality reduction by locally linear embedding." Science 290.5500 (2000): 2323-2326.

S. T. Roweis, and S. K. Lawrence. "An introduction to locally linear embedding." unpublished. Available at: http://www.cs.toronto.edu/~roweis/lle/publications.html (2000).

R. A. Horn and C. R. Johnson. "Matrix Analysis." Cambridge University Press, Cambridge, 1990

R. L. Siddon. "Fast calculation of the exact radiological path for a three-dimensional CT array." Medical physics 12. 2 (1985): 252-255.

Z. Wang, and A. C. Bovik. "A universal image quality index." Signal Processing Letters, IEEE 9.3 (2002): 81-84.

G. Wang, and M. Jiang. "Ordered-subset simultaneous algebraic reconstruction techniques (OS-SART)." Journal of X-ray Science and Technology 12.3 (2004): 169-177.

Y. E. Sidky, C. M. Kao, and X. Pan. "Accurate image reconstruction from few-views and limited-angle data in divergent-beam CT." Journal of X-ray Science and Technology 14.2 (2006): 119-139.

What is claimed is:

1. A method of reconstructing a computed tomography (CT) image, the method comprising:
    i) obtaining an initial CT image;
    ii) performing a reconstruction algorithm on the initial CT image to obtain a reconstructed image of the initial CT image;
    iii) using the reconstructed image to adjust one or more parameters associated with the image comprising using a Locally Linear Embedding (LLE) method on each of the one or more parameters;
    iv) using the adjusted one or more parameters to perform the reconstruction algorithm on the reconstructed image to obtain an updated reconstructed image; and
    v) repeating steps iii)-iv), using the most-recently updated reconstructed image in each repeated step iii), and updating the same one or more parameters in each repeated step iii) until a threshold value of a predetermined characteristic is met;

wherein the LLE method comprises:

with the K nearest vectors, representing the original data vector linearly with its neighboring vectors:

$$b_i = \sum_{k=1}^{K} w_{ik} \tilde{b}_{ik},$$

where $\tilde{b}_{ik}$ are the K nearest neighbors and $w_{ik}$ are respectively weight coefficients, and $$\sum_k w_{ik} = 1,$$

and the weight matrix can be solved by minimizing the following error:

$$\min \left\| b_i - \sum_k w_{ik} \tilde{b}_{ik} \right\|_2^2 \text{s.t.} \sum_j w_{ik} = 1,$$

and wherein, using the constraint $$\sum_k w_{ik} = 1,$$

minimizing the error is equivalent to solving the linear system:

$$\sum_k c_{jk} w_{ik} = 1,$$

where $C=(c_{jk})$ is the local covariance matrix calculated as:

$$C = (b_i - \tilde{b}_{ik})^T (b_i - \tilde{b}_{ik}).$$

2. The method according to claim 1, wherein the reconstruction algorithm is based on Total Variation (TV).

3. The method according to claim 1, wherein the LLE method includes:
    a) finding the K nearest neighbors for each high-dimensional point in terms of the Euclidean distance;
    b) representing each point linearly with its neighbors and calculating weight coefficients for its neighbors; and
    c) mapping high dimensional data with the weight coefficients to a low dimensional representation on an intrinsic manifold.

4. The method according to claim 1, wherein the LLE method includes:
    finding the K nearest neighbors of a data vector $b_i$ in its dataset vectors $\tilde{b}_{ij}$ according to the Euclidean distance:

$$d_{ij} = \|b_i - \tilde{b}_{ij}\|_2^2.$$

5. The method according to claim 1, wherein the LLE method (further) includes, calculating, with the weight coefficients $W=(w_{ik})$, the global internal coordinate $Y=(y_i)$ by solving the equation:

$$\min_{Y} \sum_{i} \left\| y_i - \sum_{k} w_{ik} y_k \right\|_2^2.$$

6. The method according to claim 5, wherein the solution of the equation that can be solved to calculate $Y=(y_i)$ is given by the bottom d+1 eigenvectors of the generalized eigenvalue problem:

$$MY=\lambda Y,$$

where $\lambda$ is the eigenvalue, and $M=(I-W)^T(I-W)$.

7. The method according to claim 1, wherein the number of nearest neighbors used in the LLE method is at least 2.

8. The method according to claim 1, wherein the LLE method includes solving the following linear system of equations:

$$Au=b_i,$$

where $u=(u_1, u_2, \ldots, u_J)$ is an image represented as a J dimensional vector, J is the number of pixels, $b_i=(b_1, b_2, \ldots, b_L)$ is data, L is the number of vector elements, and $A=(a_{jk})$ is a projection matrix related to the one or more (geometric) parameters,
wherein performing the reconstruction algorithm comprises calculating a projection matrix, which is affected by the one or more (geometric) parameters:

$$A=A(P),$$

where P is an estimated parameter vector, which includes the one or more parameters,
wherein the projections of the projection matrix are calculated using a distance-driven method,
wherein using the reconstructed image to adjust one or more parameters comprises minimizing the mean squared error between the projection data and re-projected projection data, which can be formulated as:

$$P=\arg\min \|b_i - \tilde{b}_{ij}\|_2^2 \, s.t. \, A(P)u=b_i,$$

where $b_i$ is the projection vector obtained from the measurement along different projection views, $\tilde{b}_{ij}$ is the corresponding re-projected projection vector from a reconstructed image with sampled parameters, and P is the updated vector of parameters, and
wherein the re-projected projection vector can be calculated within a densely sampled parametric range:

$$\tilde{P}_j=(p_{j1},p_{j2},\ldots,p_{jn}).$$

9. The method according to claim 8, wherein a true parameter vector is close to neighboring sampled parameter vectors, and the measured projection vector can be linearly expressed by the K nearest re-projected projection vectors associated with the sampled parameter vectors, such that:

$$b_i = \sum_{k=1}^{K} w_{ik} \tilde{b}_{ik},$$

and $$P = \sum_{k=1}^{K} w_{ik} \tilde{P}_k,$$

where $\tilde{b}_{ik}$ are the K nearest re-projection vectors associated with the corresponding K vectors of parameters $\tilde{P}_k$, and $w_{ik}$ are weight coefficients.

10. The method according to claim 1, wherein the predetermined characteristic, of which a threshold value must be met to stop repeating steps iii)-iv) is universal quality index (UQI).

11. The method according to claim 10, wherein the threshold value is at least 0.6.

12. The method according to claim 10, wherein the threshold value is at least 0.95.

13. The method according to claim 1, wherein the one or more parameters includes at least one of projection angle, source-to-object distance (SOD), object-to-detector distance (ODD), detector offset, detector tilt angle, object x-coordinate offset, object y-coordinate offset, and projection angular error.

14. The method according to claim 1, wherein obtaining the initial CT image comprises obtaining an initial parameter vector including initial value(s) for the one or more parameters associated with the image, and
wherein performing the reconstruction algorithm comprises updating the parameter vector with updated values of the one or more parameters based on the most recently reconstructed image.

15. The method according to claim 1, wherein the reconstruction algorithm comprises using an Ordered Subset Simultaneous Algebraic Reconstruction Technique (OS-SART).

16. The method according to claim 1, wherein each of step ii), step iii), step iv), and step v) is performed by a processor.

17. A computer readable medium having computer-executable instructions for performing the method according to claim 1.

18. A CT system, comprising:
an X-ray source;
a detector for detecting X-ray radiation from the X-ray source; and
a computer having the computer readable medium according to claim 17.

19. A method of reconstructing a computed tomography (CT) image, the method comprising:
i) obtaining an initial CT image;
ii) performing a reconstruction algorithm on the initial CT image to obtain a reconstructed image of the initial CT image;
iii) using the reconstructed image to adjust one or more parameters associated with the image comprising using a Locally Linear Embedding (LLE) method on each of the one or more parameters;
iv) using the adjusted one or more parameters to perform the reconstruction algorithm on the reconstructed image to obtain an updated reconstructed image; and
v) repeating steps iii)-iv), using the most-recently updated reconstructed image in each repeated step iii), and updating the same one or more parameters in each repeated step iii) until a threshold value of a predetermined characteristic is met;

wherein the LLE method comprises:
  calculating, with the weight coefficients W=($w_{ik}$), the global internal coordinate Y=($y_i$) by solving the equation:

$$\min_Y \sum_i \left\| y_i - \sum_k w_{ik} y_k \right\|_2^2.$$

20. The method according to claim 19, wherein the solution of the equation that can be solved to calculate Y=($y_i$) is given by the bottom d+1 eigenvectors of the generalized eigenvalue problem:

$$MY=\lambda Y,$$

where λ is the eigenvalue, and M=$(I-W)^T(I-W)$.

21. The method according to claim 19, wherein the LLE method further comprises:
  finding the K nearest neighbors of a data vector $b_i$ in its dataset vectors $\tilde{b}_{ij}$ according to the Euclidean distance:

$$d_{ij}=\|b_i-\tilde{b}_{ij}\|_2^2.$$

22. The method according to claim 19, wherein the LLE method further comprises:
  with the K nearest vectors, representing the original data vector linearly with its neighboring vectors:

$$b_i = \sum_{k=1}^{K} w_{ik} \tilde{b}_{ik},$$

where $\tilde{b}_{ik}$ are the K nearest neighbors and $w_{ik}$ are respectively weight coefficients, and $$\sum_k w_{ik} = 1,$$

and the weight matrix can be solved by minimizing the following error:

$$\min \left\| b_i - \sum_k w_{ik} \tilde{b}_{ik} \right\|_2^2 \text{ s.t.} \sum_j w_{ik} = 1,$$

and
  wherein, using the constraint $$\sum_k w_{ik} = 1,$$

minimizing the error is equivalent to solving the linear system:

$$\sum_k c_{jk} w_{ik} = 1,$$

where C=($c_{jk}$) is the local covariance matrix calculated as:

$$C=(b_i-\tilde{b}_{ik})^T(b_i-\tilde{b}_{ik}).$$

23. The method of claim 19, wherein the LLE method further comprises solving the following linear system of equations:

$$Au=b_i,$$

where u=($u_1, u_2, \ldots, u_J$) is an image represented as a J dimensional vector, J is the number of pixels, $b_i$=($b_1, b_2, \ldots, b_L$) is data, L is the number of vector elements, and A=($a_{jk}$) is a projection matrix related to the one or more (geometric) parameters,
  wherein performing the reconstruction algorithm comprises calculating a projection matrix, which is affected by the one or more (geometric) parameters:

$$A=A(P),$$

where P is an estimated parameter vector, which includes the one or more parameters,
  wherein the projections of the projection matrix are calculated using a distance-driven method,
  wherein using the reconstructed image to adjust one or more parameters comprises minimizing the mean squared error between the projection data and re-projected projection data, which can be formulated as:

$$P=\arg\min\|b_i-\tilde{b}_{ij}\|_2^2 \text{ s.t. } A(P)u=b_i,$$

where $b_i$ is the projection vector obtained from the measurement along different projection views, $\tilde{b}_{ij}$ is the corresponding re-projected projection vector from a reconstructed image with sampled parameters, and P is the updated vector of parameters, and
  wherein the re-projected projection vector can be calculated by the equations provide in claims 8 within a densely sampled parametric range:

$$\tilde{P}_j=(p_{j1},p_{j2},\ldots,p_{jn}).$$

24. The method according to claim 23, wherein a true parameter vector is close to neighboring sampled parameter vectors, and the measured projection vector can be linearly expressed by the K nearest re-projected projection vectors associated with the sampled parameter vectors, such that:

$$b_i = \sum_{k=1}^{K} w_{ik} \tilde{b}_{ik}, \text{ and}$$

$$P = \sum_{k=1}^{K} w_{ik} \tilde{P}_k,$$

where $\tilde{b}_{ik}$ are the K nearest re-projection vectors associated with the corresponding K vectors of parameters $\tilde{P}_k$, and $w_{ik}$ are weight coefficients.

25. A method of reconstructing a computed tomography (CT) image, the method comprising:
  i) obtaining an initial CT image;
  ii) performing a reconstruction algorithm on the initial CT image to obtain a reconstructed image of the initial CT image;
  iii) using the reconstructed image to adjust one or more parameters associated with the image comprising using a Locally Linear Embedding (LLE) method on each of the one or more parameters;
  iv) using the adjusted one or more parameters to perform the reconstruction algorithm on the reconstructed image to obtain an updated reconstructed image; and
  v) repeating steps iii)-iv), using the most-recently updated reconstructed image in each repeated step iii), and updating the same one or more parameters in each repeated step iii) until a threshold value of a predetermined characteristic is met;

wherein the LLE method comprises solving the following linear system of equations:

$$Au=b_i,$$

where $u=(u_1, u_2, \ldots, u_J)$ is an image represented as a J dimensional vector, J is the number of pixels, $b_i=(b_1, b_2, \ldots, b_L)$ is data, L is the number of vector elements, and $A=(a_{jk})$ is a projection matrix related to the one or more (geometric) parameters, wherein performing the reconstruction algorithm comprises calculating a projection matrix, which is affected by the one or more (geometric) parameters:

$$A=A(P),$$

where P is an estimated parameter vector, which includes the one or more parameters, wherein the projections of the projection matrix are calculated using a distance-driven method, wherein using the reconstructed image to adjust one or more parameters comprises minimizing the mean squared error between the projection data and re-projected projection data, which can be formulated as:

$$P=\arg\min\|b_i-\tilde{b}_{ij}\|_2^2 \text{ s.t. } A(P)u=b_i,$$

where $b_i$ is the projection vector obtained from the measurement along different projection views, $\tilde{b}_{ij}$ is the corresponding re-projected projection vector from a reconstructed image with sampled parameters, and P is the updated vector of parameters, and wherein the re-projected projection vector can be calculated within a densely sampled parametric range:

$$\tilde{P}_j=(p_{j1},p_{j2},\ldots,p_{jn}).$$

26. The method according to claim 25, wherein a true parameter vector is close to neighboring sampled parameter vectors, and the measured projection vector can be linearly expressed by the K nearest re-projected projection vectors associated with the sampled parameter vectors, such that:

$$b_i = \sum_{k=1}^{K} w_{ik} \tilde{b}_{ik}, \text{ and}$$

$$P = \sum_{k=1}^{K} w_{ik} \tilde{P}_k,$$

where $\tilde{b}_{ik}$ are the K nearest re-projection vectors associated with the corresponding K vectors of parameters $\tilde{P}_k$, and $w_{ik}$ are weight coefficients.

27. The method according to claim 25, wherein the LLE method further comprises:

finding the K nearest neighbors of a data vector $b_i$ in its dataset vectors $\tilde{b}_{ij}$ according to the Euclidean distance:

$$d_{ij}=\|b_i-\tilde{b}_{ij}\|_2^2.$$

28. The method according to claim 25, wherein the LLE method further comprises:

with the K nearest vectors, representing the original data vector linearly with its neighboring vectors:

$$b_i = \sum_{k=1}^{K} w_{ik} \tilde{b}_{ik},$$

where $\tilde{b}_{ik}$ are the K nearest neighbors and $w_{ik}$ are respectively weight coefficients, and $$\sum_k w_{ik} = 1,$$

and the weight matrix can be solved by minimizing the following error:

$$\min \left\| b_i - \sum_k w_{ik} \tilde{b}_{ik} \right\|_2^2 \text{ s.t.} \sum_j w_{ik} = 1,$$

and wherein, using the constraint $$\sum_k w_{ik} = 1,$$

minimizing the error is equivalent to solving the linear system:

$$\sum_k c_{jk} w_{ik} = 1,$$

where $C=(c_{jk})$ is the local covariance matrix calculated as:
$$C=(b_i-\tilde{b}_{ik})^T(b_i-\tilde{b}_{ik}).$$

29. The method according to claim 25, wherein the LLE method further comprises, calculating, with the weight coefficients $W=(w_{ik})$, the global internal coordinate $Y=(y_i)$ by solving the equation:

$$\min_Y \sum_i \left\| y_i - \sum_k w_{ik} y_k \right\|_2^2.$$

30. The method according to claim 29, wherein the solution of the equation that can be solved to calculate $Y=(y_i)$ is given by the bottom d+1 eigenvectors of the generalized eigenvalue problem:

$$MY=\lambda Y,$$

where $\lambda$ is the eigenvalue, and $M=(I-W)^T(I-W)$.

* * * * *